United States Patent [19]
Torrisi et al.

[11] Patent Number: 5,703,927
[45] Date of Patent: *Dec. 30, 1997

[54] SAFETY RING FOR DOUBLE OPEN-ENDED SAMPLE HOLDER CELL FOR SPECTROSCOPIC ANALYSIS

[75] Inventors: Angelo M. Torrisi, 10 Anpell Dr., Scarsdale, N.Y. 10583; Roland Urbano, Tuckahoe, N.Y.

[73] Assignee: Angelo M. Torrisi, Scarsdale, N.Y.

[*] Notice: The term of this patent shall not extend beyond the expiration date of Pat. No. 5,351,281.

[21] Appl. No.: 549,832

[22] PCT Filed: Apr. 14, 1994

[86] PCT No.: PCT/US94/04116

§ 371 Date: Oct. 13, 1995

§ 102(e) Date: Oct. 13, 1995

[87] PCT Pub. No.: WO94/24547

PCT Pub. Date: Oct. 27, 1994

Related U.S. Application Data

[63] Continuation-in-part of Ser. No. 47,315, Apr. 15, 1993, Pat. No. 5,351,281.

[51] Int. Cl.[6] ............................................. H05G 1/00
[52] U.S. Cl. ............................................. 378/208; 378/79

[58] Field of Search ............................... 378/208, 79, 80, 378/45, 47

[56] References Cited

U.S. PATENT DOCUMENTS 5,253,280  10/1993  Mizuta ....................... 378/208
5,351,281  9/1994   Torrisi et al. ................ 378/79

Primary Examiner—Don Wong
Attorney, Agent, or Firm—Paul J. Sutton

[57] ABSTRACT

This invention relates to a double open-ended sample holder cell for x-ray spectroscopic analysis including a cell (58) for containing the sample, a first ring (52) mounted to the cell at one open face (48) securing an analytic film (56) to the cell, a second ring (50) mounted to the cell securing a microporous or solid film (54) at the other open face (46); the second ring including a continuous ring wall extending outwardly from the rim o the cell; the continuous ring wall and the microporous film defining a compartment adjoining the second open face that contains any sample material that passes or breaks through the microporous or solid film. A support bar (92) connected to the top securing ring provides a grip for a tool used in the process of remotely raising or lowering the sample holder relative to placement into or removal from an x-ray cassette.

5 Claims, 14 Drawing Sheets

X-RAY SOURCE     X-RAY DECTECTOR

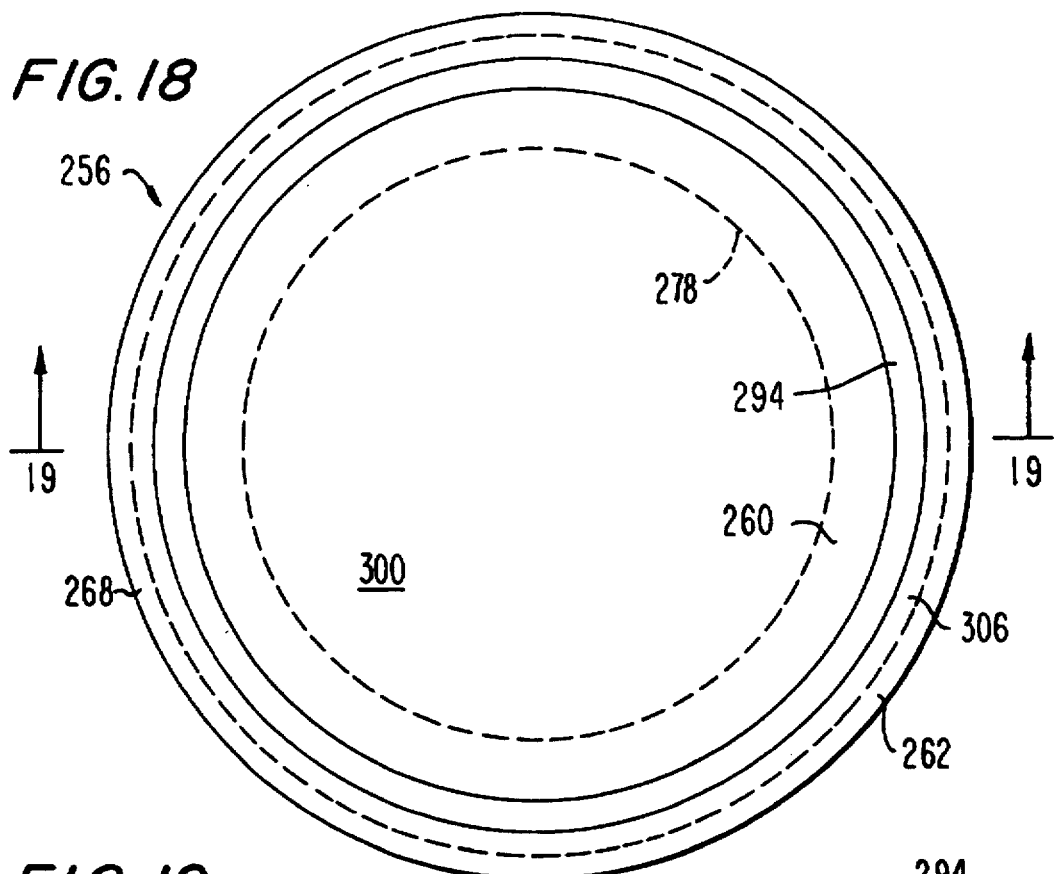
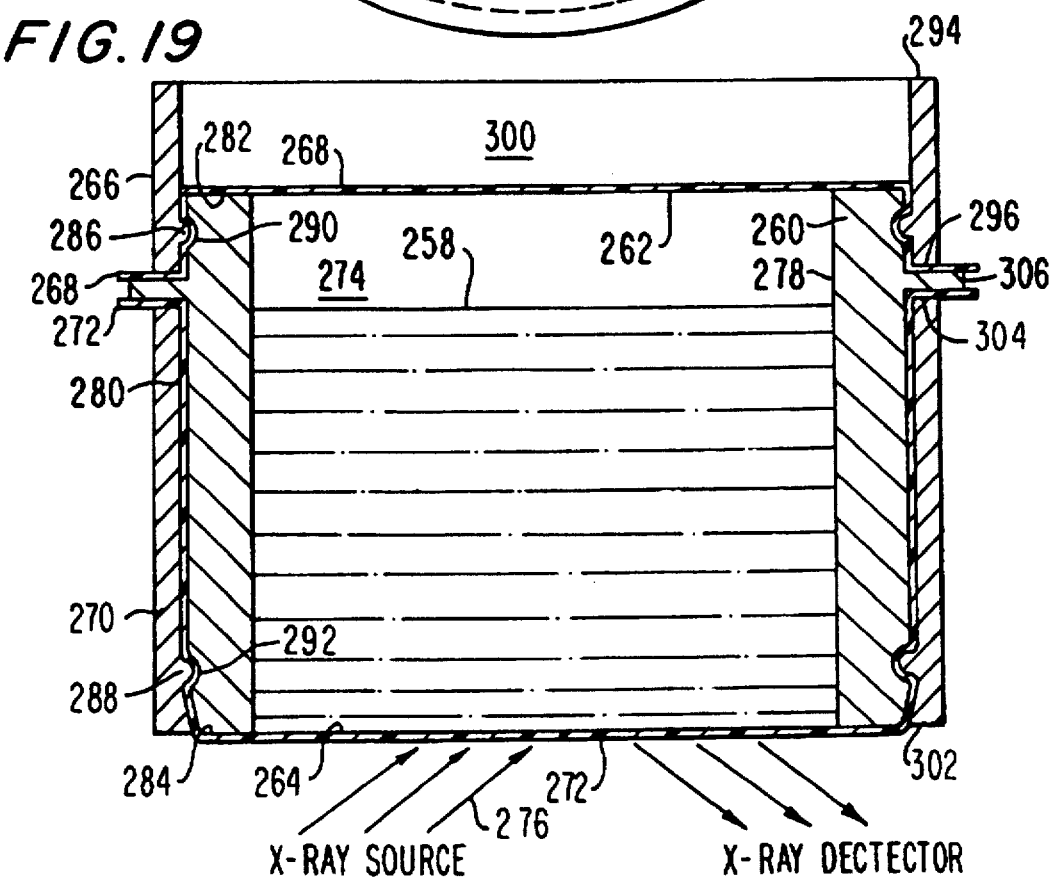

SAFETY RING FOR DOUBLE OPEN-ENDED SAMPLE HOLDER CELL FOR SPECTROSCOPIC ANALYSIS

This application is a continuation-in-part of application Ser. No. 8/047,315 entitled "Handling Support for Sample Holder for X-ray Spectroscopic Analysis", filed Apr. 15, 1993 now U.S. Pat. No. 5,351,281.

FIELD OF THE INVENTION

This invention relates generally to the field of disposable sample holders for X-ray spectroscopic analysis and more particularly to a handling support for safe and efficient handling of the sample holders.

This invention also relates to a safety ring mounting a microporous film across one face of a double open-ended sample holder cell for X-ray spectroscopic analysis for the purpose of providing safe and efficient use of the sample holder.

BACKGROUND OF THE INVENTION

The field of X-ray spectroscopy involves the measurement of the spectra of certain material being analyzed. Generally, the sample material being analyzed may be any liquid, slurry, powder material, or industrial gas that can occur in the run of industry. A sample is positioned in a cylindrical sample holder that includes a holder body forming a cell adapted to contain the sample. A disposable sample holder is generally made of plastic and is generally disposed of after a single use. A sample holder generally ranges in size between diameters of 20 to 57 mm and in height about 25 to 35 mm.

Sample holders include single open-ended cylindrical body type cells and double open-ended cylindrical body cells. For the double open-ended cell, a very thin plastic analytic film is placed as an X-ray transparent window across one of the circular end faces of the body of the holder, and the skirt of the film is then secured by a plastic securing ring to the outer wall of the body and the analytic film becomes taut. The body is then inverted so that the window face is positioned downwards. Alternatively, the plastic securing ring and the thin plastic analytic film is placed into a well of a sample holder film assembly device and one of the circular end faces of the holder body is placed over the film and the skirt of the film is then secured by the plastic ring to the outer wall of the body so that the analytic film becomes taut. The latter method is described in our U.S. Pat. No. 4,587,656. It is noted that the plastic securing rings are made of a thin, plastic, flexible material so that the thin analytic film can be gently yet firmly secured to the sample holder body. A double open-ended sample holder is illustrated in FIGS. 1 and 2 and discussed in relation therewith below.

In each of the above-described assembly methods, one circular end face is open so as to form a holder cell. The holder cell is then filled with the sample through the top open face of the cell. The sample may be a benign substance or it may be noxious, contaminated, caustic, or offensive. In addition, the sample may be treated with a solvent to dissolve the sample, the solvent itself being noxious.

After the sample material to be analyzed has been loaded into the sample cell and otherwise prepared for X-ray analysis, the cell is loaded into an X-ray sample cassette that is then moved into position for bombardment by X-rays. X-ray cassettes are cylindrical holders defining chambers into which the sample holder cell is loaded. Generally, the chambers of the cassettes have top edges that are of greater height than the height of the top edges of the sample holder cells. In addition, the diameters of the cassettes are generally only slightly greater than the diameters of the sample holders so that little space is provided between the wall of the cassette and the wall of the sample holder. Cassettes often have a spring-loaded screw-on cap over the cell.

In the present state of the art, a double open-ended sample holder is loaded into an X-ray cassette by hand by a technician. More in detail, the double open-ended cell is picked up by the technician, who may or may not be wearing protective gloves, transferred to a position above the cassette, and hand placed into the cassette. Also, the cassette may be located for loading purposes in an isolation chamber in which the double open-ended sample holder is placed into the cassette by a technician who manipulates the holder with flexible gloves that extend into the chamber.

In the process of X-ray analysis, when X-rays are directed at the bottom end of the cell body through the analytic film at the sample inside; the X-ray cause heat to be generated within the sample material. Many substances will not generate gases or vapors, or if they do so, such gases or vapors may be harmless to the X-ray equipment or the immediate environment. Certain sample substances, usually a liquid but at times a powder, upon heating will generate a vapor or a gas containing particles originating from the sample substance that should not be allowed to contaminate the X-ray machine or pass into the surrounding area. In such cases, the upper open face of the cell body must be covered to prevent passage of such contaminants. A problem exists, however, in that simple covering of the open face with a sheet of plastic film secured by a securing top ring or by a plastic cap will result in the sealing of the cell body so that a buildup of pressure within the cell body will occur upon generation of vapors therein. Such a pressure buildup will result in the bottom analytic film bulging outwardly from the cell along with the sample material thus distorting the entire process of the X-ray analysis.

In such cases where a top seal of the sample holder is required to prevent passage of vapor borne contaminants, a microporous film is secured across the top face of the cell body secured thereto by an upper securing ring. The microporous film will pass gases generated by the heated sample material but will filter out particles that would cause harm to the surrounding environment.

Microporous film is a gas permeable material, generally polypropylene or teflon, specifically intended to establish and maintain pressure equalization within a sample holder cell. Such film is characterized with the property of containing tortuous submicron-size passageways extending from one surface side to the other. This permits gases and vapors to permeate yet simultaneously prohibits the penetration of particles of the sample substance therethrough. Microporous film enables evacuation of entrapped gases through the micropores while at the same time relieves the sample holder of vapor pressure buildup. Under inert gas conditions such as helium, the micropores function as passageways for the gas to enter the sample holder cell and purge out any entrapped gases or vapors. In atmospheric operating conditions, the film helps maintain pressure equalization by continuously allowing the exchange of contained gases with the surrounding air environment. In all cases the immediate important consideration is to maintain a taut, thin-film sample support plane that defines the surface of the contained solution or powdered sample material. Any distension or convolution of the thin-film substance affects the sample-to-excitation source distance implying higher or lower than actual analytic concentration values.

In each of these cases the sample cell holder is in effect dropped into the cassette. This procedure is undesirable since the entire handling procedure for sample analysis requires gentle handling of the sample throughout the entire procedure of X-ray analysis, which includes gentle placement of the sample cell into the cassette.

Even greater problems occur with the removal of the sample holder cell from the X-ray cassette after the X-ray analysis. When the sample substances are noxious or offensive, spilling of the substances during removal of the cell from the cassette and during its transit to either a waste disposal station or to a recovery station often has undesirable results.

Remote handling caps for sample holders exist in the art, but not for microporous film covered holders. For example, our U.S. Pat. No. 4,575,869 describes a sample holder that includes a handling support for safe handling of the sample holder by either local or remote means. This handling support does not cover the case of a double open-ended cell where the top face of the cell must be covered by a microporous film. The top wall of remote handling caps also would be in proximity or in contact with the microporous film so that the integrity of the microporous film would be compromised.

Another aspect of X-ray spectroscopic analytic analysis is set forth as follows. X-ray spectroscopic apparatuses are generally designed with inverted optics, that is, with the X-ray excitation source located beneath the sample holder; application of the X-ray beam will generate heat in the sample material and cause out-gassing and/or expansion of the sample material. When a double open-ended sample holder is used, a thin analytic film is placed across the open bottom face and the sample material, either a liquid or a powder, is poured into the sample holder to the depth needed for analysis. The sample substance is gravity supported upon the film with the analytic plane being defined along the analytic film. The analytic plane of the sample material is then bombarded with X-rays. The top face of the cell can either be open or be closed by a microporous or a solid film, with the selection of an open or a closed top face being dependent upon the type of substance being analyzed and negative or positive pressure in the cassette sample holder.

Microporous film is used to close the top face to allow escape of gases but to repel the passage of liquid or solid substances contained in the sample. Thus, any gas created within the heated liquid can rise from the liquid to the area between the microporous film and the top surface of the sample and ultimately pass through the microporous film into the chamber of the cassette holder, which can be at either atmospheric or negative pressure, while simultaneously preventing passage of liquids or solids. This result both a) prevents distortion of the bottom analytic plane of the thin film and so maintains the integrity of the analytic process, which demands a constant level plane at the bottom analytic surface, and b) filters out substances from the gases that are passed through the microporous film.

Certain microporous film may not be phobic to all liquids and can pass certain liquids, for example, oils. Such liquids upon heating during analysis flow across the outer surface of the microporous film and ultimately from the film onto the sample holder and sample holder cassette and ultimately onto the X-ray apparatus. Contamination of the X-ray apparatus is highly undesirable.

Solid film is used to close the top face to control liquid, vapor, gas, or powder in any environment, that is, in a vacuum, inert gas, or air. At times, solid film is deliberately punctured by the operator for venting in order to equalize pressures. If during the analysis process, liquids unanticipatedly pass through the venting aperture, contamination of the X-ray apparatus can occur.

Also, either microporous or solid film can rupture during the analysis process; such breakage can result in contamination of the X-ray analysis.

The state of the prior art of double open-ended sample cells is shown in FIGS. 14 and 14A, which are described below in the detailed description.

X-ray spectroscopic analytic apparatuses are also at times designed with upright optics, that is, with the X-ray excitation source located above a double open-ended sample holder. An analytic-plane thin film is located at the top of the sample holder and a microporous film is located at the bottom of the sample holder; for this type of analysis, only microporous film is used. The sample substance is placed in the sample holder in such a manner that the substance completely fills the sample holder to the level of the top analytic-plane thin film in order to maintain the integrity of the analytic plane and to ensure scientifically consistent results. The upright optics sample holder is located in a cassette in preparation for upright optics analysis. The cassette maintains the sample cell close to the X-ray source by means of a spring mechanism. The full force of the spring-powered pressure plate of the cassette cap is directed against the entire area of the bottom side microporous film. Escape of heat-generated gases through the microporous film from the sample holder is resisted by the bottom pressure plate with the result that build-up of pressure from the heat-generated gases in the sample holder prevents expansion of the microporous film. Because of the lesser tensile strength of the microporous film relative to the analytic-surface thin film, a pressure buildup in the sample holder can result in rupture of the microporous film at concentrated pressure point irregularities at the pressure plate. When a rupture of the bottom microporous film occurs, the sample substance will spill not only into the cassette holder but could also contaminate the X-ray apparatus.

SUMMARY OF THE INVENTION

The present invention contemplates a double open-ended sample holder for X-ray spectroscopic analysis of sample materials contained therein that have the top open end of the sample holder covered by a microporous film that overcomes the limitations and disadvantages of the prior art by providing a double open-ended sample holder with a handling support that meets the special needs of handling double open-ended sample cell holders directly by a technician with a remote handling tool (tweezers), or by a remote precision handling tool (a robot).

It is therefore an object of the present invention to provide a double open-ended sample holder containing sample material requiring a microporous film that allows gentle or remote handling of the sample holder relative to its placement into or removal from an X-ray cassette.

It is another object of the present invention to provide a double open-ended sample holder having a microporous film mounted across its top open face that includes a remote handling support that allows the microporous film to pass gases generated in the cell at a maximum rate of evacuation but prevents passage of harmful materials.

In accordance with these and other objects that will become apparent in the course of this disclosure, there is provided a double open-ended sample holder for sample material for X-ray spectroscopic analysis including a cylindrical body cell containing the sample material and having top and bottom open faces. An analytic film is positioned across the lower face and a microporous film positioned across the upper face cell passes gases generated by X-rays striking the sample material but does not pass harmful materials contained in the cell. Upper and lower rings mounted to the cylindrical body secure the lower and upper films to the body. A handling support connected to the top securing ring provides a grip for a tool used in the process of remotely raising or lowering the sample holder relative to placement into or removal from an X-ray cassette. The handling support is spaced from the microporous film so that gases generated in the cell are allowed to escape across the entire area of the film at a maximum rate of evacuation.

The present invention also contemplates a double open-ended sample holder for X-ray spectroscopic analysis of sample materials contained therein that includes a microporous or a solid film mounted across one open face of the sample holder that includes means for preventing contamination of the X-ray apparatus in either the event that the film breaks or the event that along with the gases certain liquid or solid substances pass or break through the microporous or the solid film.

The present invention also contemplates a double open-ended sample holder for X-ray spectroscopic analysis of sample materials contained therein in an inverted optics position that includes a ring securing a microporous or solid film across the top face of the sample holder which has a cylindrical wall that together with the microporous or solid film defines a compartment that retains overflow sample material in the compartment, thus protecting the X-ray apparatus from contamination.

The present invention also contemplates a double open-ended sample holder for X-ray spectroscopic analysis of sample materials contained therein in an upright optics position that includes a microporous film secured to the cell body by a ring which includes a cylindrical wall that together with the microporous film defines a compartment that allows expansion of the bottom microporous film into the compartment when gases are generated in the sample material and that includes an upright cup which is positioned in the compartment and which holds the sample holder, thus providing a container for preventing escaping substances from contaminating the X-ray apparatus.

In accordance with these and other objects that will become apparent in the course of this disclosure, there is provided a sample holder for a sample material for X-ray spectroscopic analysis, comprising a cylindrical cell for containing the sample material and having first and second rims defining opposed first and second open faces, respectively; a first ring mounted to the cell at the first open face; an analytic film secured to the cell by the first ring across the first open face; a second ring mounted to the cell at the second open face, the second ring including a continuous ring wall extending outwardly from the second rim perpendicular to the second open face; and a protective microporous or solid film secured to the cell by the second ring across the second open face; the continuous ring wall and the protective film defining a reservoir, or compartment, adjoining the second open face. Optionally provided is a handling support for providing a grip for a tool used in the process of raising or lowering the sample holder, the handling support being connected to the second ring and spaced away from the protective microporous or solid film.

The sample holder can be used for both inverted and upright optics X-ray analysis systems. In the case of an upright optics analysis system, the sample holder is positioned in a cassette holder, or container, having opposed first and second sides with the first side being open and the second side defining an aperture, the container including: a cap having inner and outer cap surfaces removably connected to the container at the first side; a pressure plate; and a spring or other biasing means connected to the cap inner surface and to the pressure plate, the spring being for upwardly pressuring the pressure plate. The sample holder for upright optics analysis has the analytic film located in an upside position during analysis proximate to the aperture and the microporous film located in a downside position. The present invention for upright optics analysis includes a cup having a cup bottom wall with a cup rim and a continuous upright cup wall connected to the cup bottom rim, the cup wall and bottom wall defining a cup chamber, the sample holder being positioned in the upright cup chamber with the continuous wall of the second ring being in contact with the cup bottom wall and the pressure plate being in pressure contact with the cup bottom wall, whereby the microporous film can expand into the cup chamber during X-ray analysis, and in the event the microporous film breaks during X-ray analysis, the sample material will spill into and be contained in the cup chamber.

A prior art sample holder occasionally used is illustrated in FIGS. 15 and 15A, which is described below in the Detailed Description. This type of sample holder includes a closed top with vent holes punched therethrough and including a cylindrical wall defining a reservoir, or compartment, for containing substances escaping from the cell. The disadvantage of the latter sample holder is that the technician must first load the holder in an inverted, or bottom load, position, then invert the sample holder to an upright position, and finally punch vent holes through the top wall of the sample holder. This process is particularly a problem when the sample holder is full. Mishaps are always a possibility. In addition, this type of sample holder does not employ any microporous film and substances are free to pass through the punch holes.

The present invention can be better understood and the objects and important features, other than those specifically set forth above, will become apparent when consideration is given to the following details and description, which when taken in conjunction with the annexed drawings, describes, discloses, illustrates, and shows preferred embodiments or modification of the present invention and what is presently considered and believed to be the best mode of practice in the principles thereof.

A BRIEF STATEMENT OF THE FIGURES

FIG. 18 illustrates a top plan view of a double open-ended sample holder with a ring mounting a protective microporous or solid film in accordance with the present invention of the ring defining a compartment;

FIG. 19 is a view taken through line 19—19 of FIG. 16;

DETAILED DESCRIPTION OF THE PREFERRED EMBODIMENT

Reference is now made in detail to the drawings wherein the same numerals refer to the same or similar elements throughout.

Figure 1:
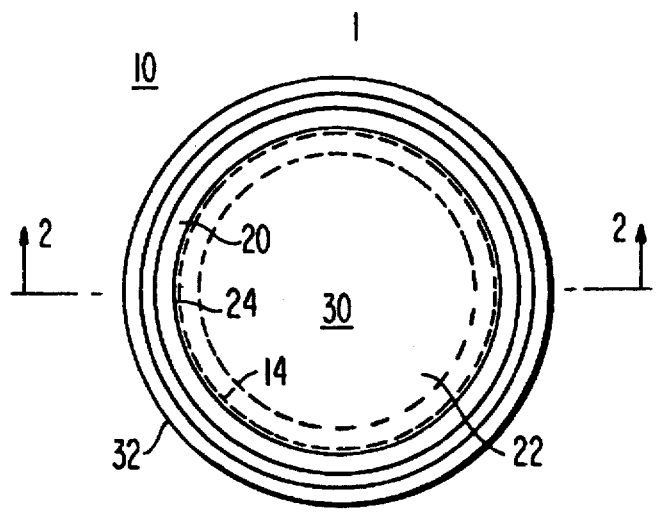
FIG. 1 illustrates a prior art double open-ended sample holder in a top view.
Figure 2:
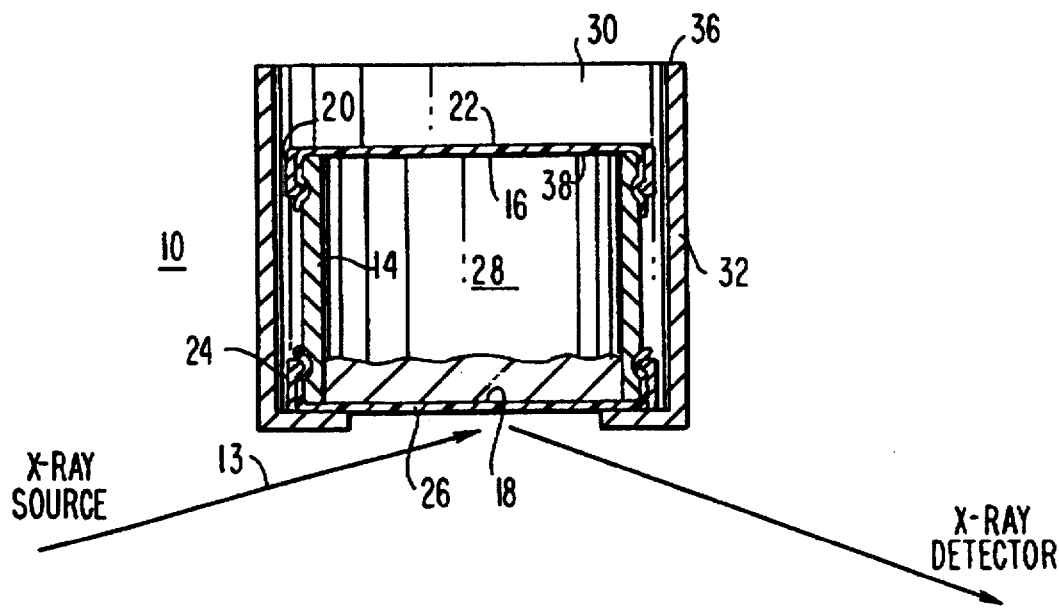
FIG. 2 is a sectional view taken through line 2—2 of FIG. 1.

A prior art double open-ended sample holder 10 holding sample material 12 which can be a liquid or powder, shown here as a powder, for X-ray spectroscopic analysis is illustrated in FIGS. 1 and 2. Sample material 12 is of a nature that X-rays 13 generate heat therein resulting in the creation of a gas containing contaminants that must not be allowed to pass from sample holder 10. At the same time, a pressure buildup in sample holder 10 must be avoided. Sample holder 10 includes a cylindrical wall 14 having a top open face 16 and an opposed bottom open face 18 and an upper cylindrical ring 20 securing an upper thin plastic microporous film 22 to wall 14 across top open face 16 and a lower cylindrical ring 24 securing a lower thin plastic analytic film 26 across bottom face 18 so as to define a sample holder cell 28.

Sample holder 10 is positioned in the cylindrical compartment 30 of an X-ray cassette 32 for an X-ray spectroscopic apparatus with X-rays 13 entering through lower analytic film 26 to strike sample material 12 at an angle and returning to the X-ray detector for analysis. Cassette 32 usually has a circular upper rim 36 that is located above the circular upper rim 38 of body wall 14 as shown in FIG. 2, or located at an equal level with upper rim 38. Lowering and raising sample holder 10 into cassette 32 presents a problem of protection of the technician or the X-ray apparatus.

Figure 3:
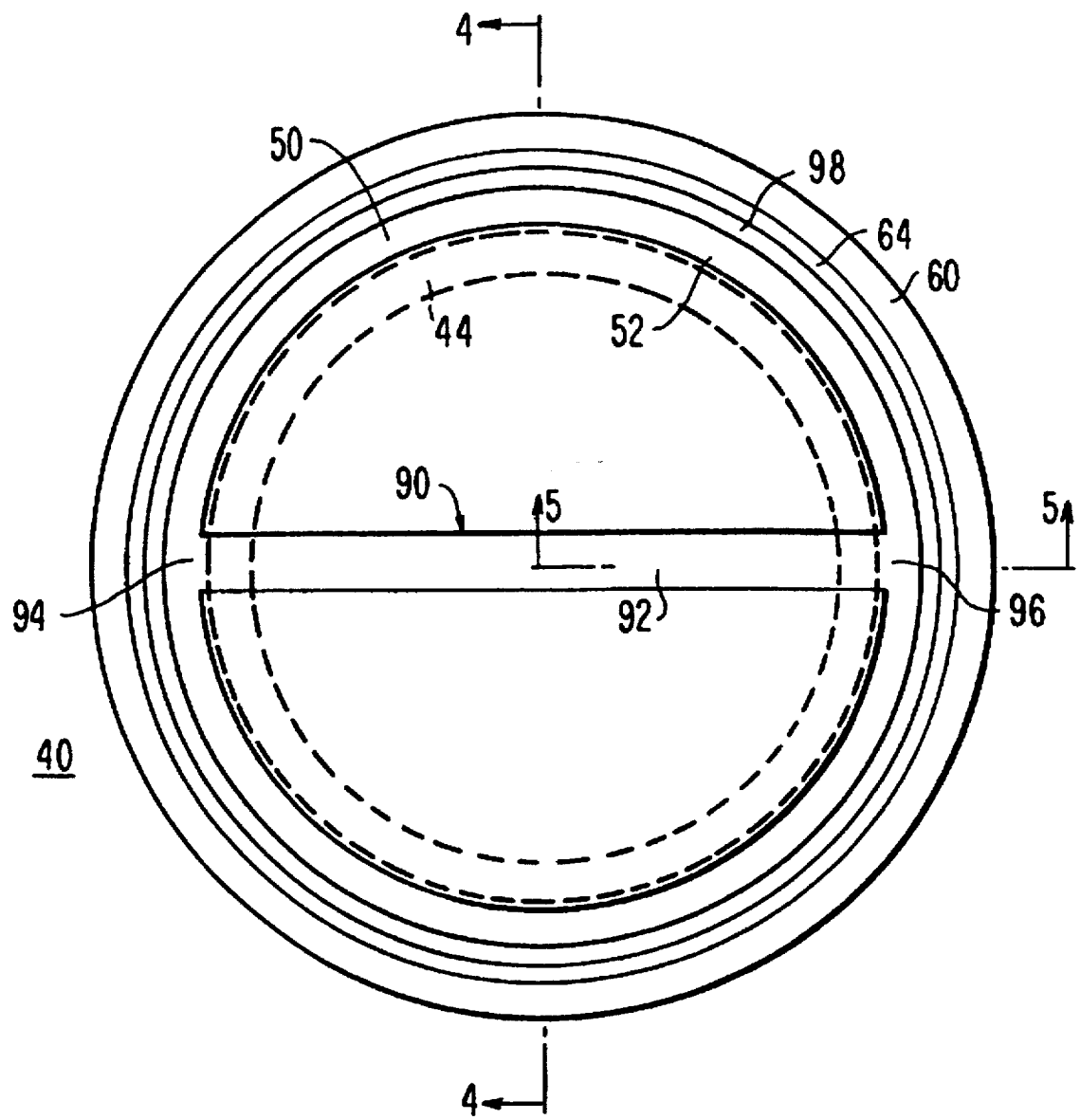
FIG. 3. illustrates a top view of a double open-ended sample holder in accordance with the present invention.
Figure 4:
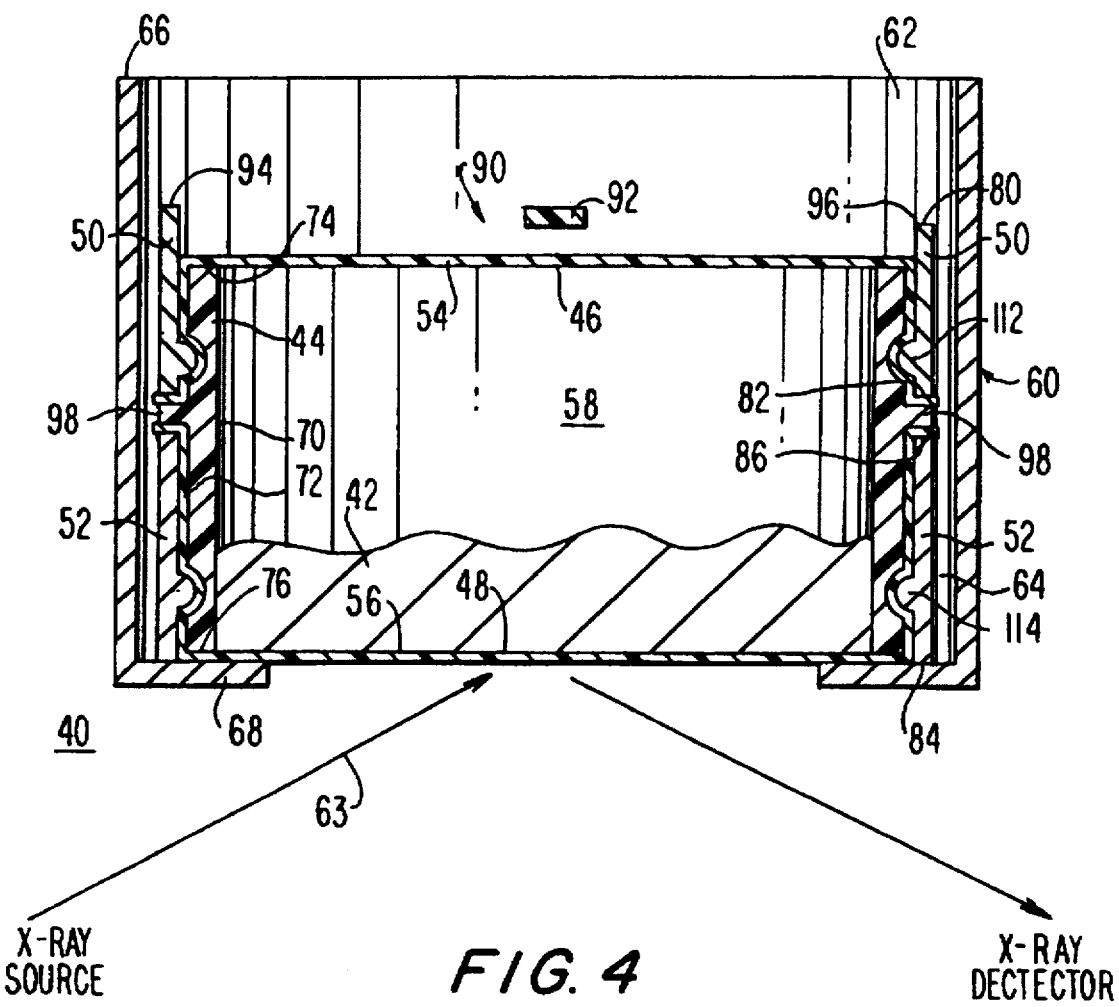
FIG. 4 is a sectional view taken through line 4—4 of FIG. 3.
Figure 5:
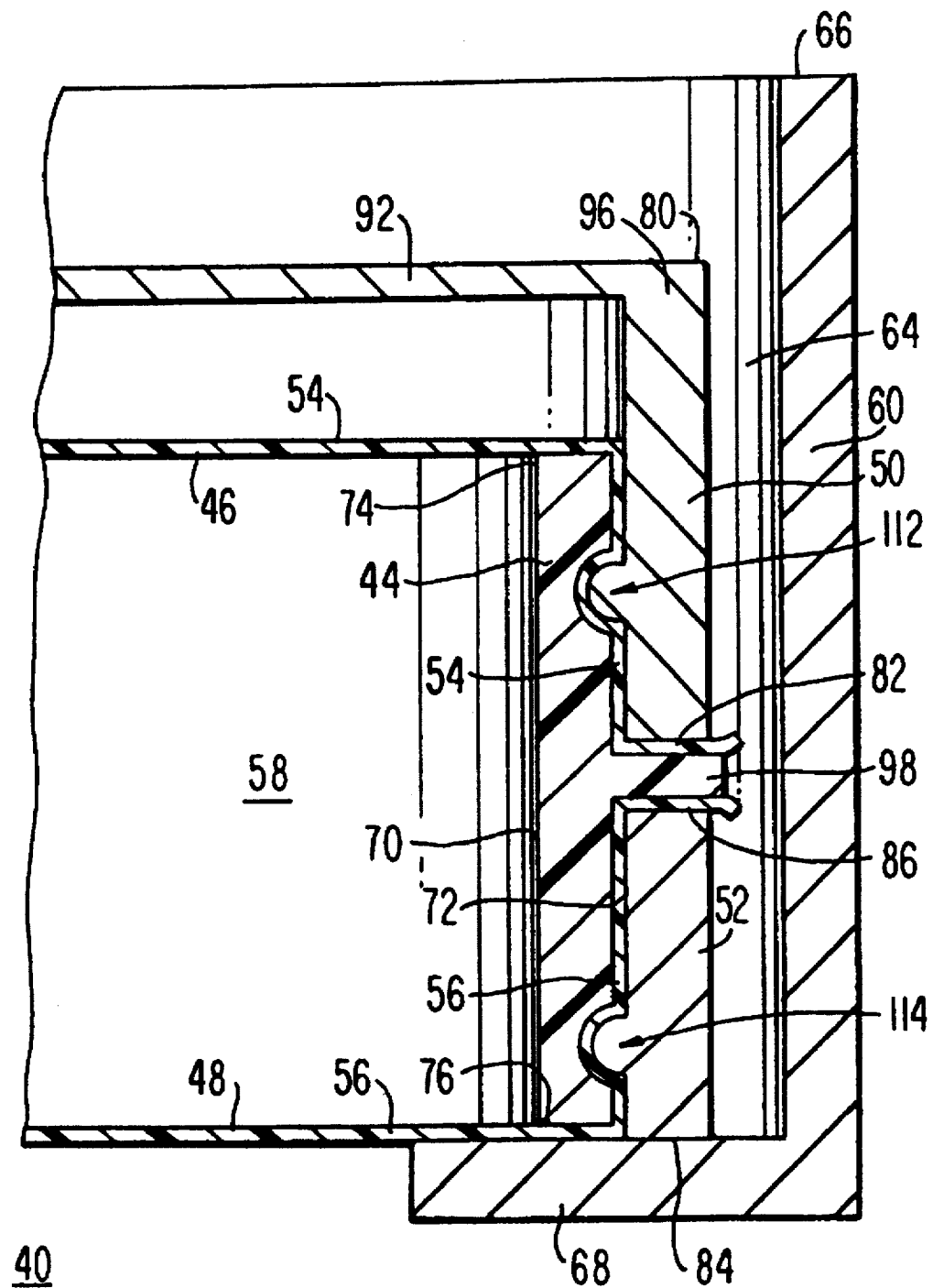
FIG. 5 is a sectional view taken through line 5—5 of FIG. 4.

In accordance with the present invention, a double open-ended sample holder 40 holding sample material 42 which can be a liquid or powder, shown here as a powder, for X-ray spectroscopic analysis is illustrated in FIGS. 3, 4, and 5. Sample holder 40 includes a cylindrical cell wall 44 having a top open face 46 and an opposed bottom open face 48 and an upper cylindrical ring 50 securing an upper microporous film 54 across top open face 46 of cell wall 44 and a lower cylindrical ring 52 securing a lower analytic film 56 tautly across bottom open face 48 of cell wall 44 so as to define a sample holder cell 58. Sample holder 40 is positioned in a cassette 60 for an X-ray spectroscopic apparatus, specifically in the cassette compartment 62, with X-rays 63 entering through analytic film 56 to strike sample material 42 at an angle and returning to the X-ray detector for analysis. Sample holder 40 is positioned in cassette 60 with upper and lower rings 50 and 52 and cassette 60 having a space 64 therebetween. Cassette 60 has a circular upper rim 66 and a circular lower flange 68 extending inwardly from the circular bottom end of cassette 60. Flange 68 has an inner flange diameter that is less than the outer diameter of sample holder 40 so that sample holder 40 rests upon flange 68 when positioned in cassette 60. Flange 68 defines a circular open area across the flange diameter for passage of X-rays 63 to bottom open face 48 of cell wall 44.

Cylindrical cell wall 44 has inner and outer surfaces 70 and 72, respectively, and opposed circular top and bottom wall rims 74 and 76, respectively, that define opposed top and bottom faces 46 and 48, respectively. Upper microporous film 54, which is positioned across top open face 46 of cell 58, passes gas from cell 58 resulting from heat generated in sample material 42 by X-rays 63 and simultaneously prevents harmful particle materials from passing out of cell 58. Lower analytic film 56 is positioned across bottom open face 48 of cell 58 and lower ring 52 maintains a taut film surface for sample material 42 in contact therewith for X-ray analysis.

Upper ring 50 is mounted to cell wall 44 at outer surface 72. Upper ring 50 has upper ring circular outer and inner rims 80 and 82, respectively. Upper ring outer rim 80 is spaced above circular top wall rim 74. Upper ring 50 mounts microporous film 54 to cell wall 44 wherein microporous film 54 extends across top open face 46 and is pressed between outer surface 72 and the inner surface of upper ring 50. Lower ring 52 mounts analytic film 56 to cell wall 44 wherein analytic film 56 extends across bottom open face 48 and is pressed between outer surface 72 of cell wall 44 and the inner surface of lower ring 52. Lower ring 52 has outer and inner rims 84 and 86, respectively, with outer rim 84 being generally aligned with bottom wall rim 76 and bottom open face 48.

A handling support 90 is connected to upper ring outer rim 80 and spaced above top face 46 of cell 58. Handling support 90 provides a grip for a tool used in the process of gentle placement or removal of sample holder 40 from cassette 60, that is, lowering or raising sample holder 40.

Handling support 90 includes a support bar 92 attached at opposed ends 94 and 96 to upper ring outer rim 80 extending diametrically across and horizontally spaced above top face 46 of cell 58 so that the entire area of microporous film 54 is available to pass gases generated by X-rays 63 striking sample material 42 in cell 58. In addition, support bar 92 is spaced at a distance above microporous film 54 without interfering with the integrity of the face of microporous film 54. In addition, support bar 92 is spaced at a distance above microporous film 54 sufficient to allow a tool to be positioned under bar 92.

A circular stop flange 98 extending outwardly from outer surface 72 of cylindrical cell wall 44 seats upper ring 50 at inner rim 82 relative to cell wall 44 during the mounting process and in addition prevents movement in an axial direction towards bottom face 48 after seating. Stop flange 98 also seats lower ring 52 at inner rim 86 relative to cell wall 44 during the mounting process and in addition prevents axial movement in a direction towards top face 46 after seating.

Inner rim 82 of upper ring 50 is spaced at such a distance from outer rim 80 and is of such a thinness that inner rim 82 is both flexible and resilient so that microporous film 54 can be mounted to said cell wall 44 gently and securely without being damaged or torn. Lower ring 52 has both the flexibility and resilience to gently mount analytic film 56 and to hold analytic film 56 firmly and tautly across bottom face 48. Upper and lower rings 50 and 52 are made of resilient plastic.

Figure 6:
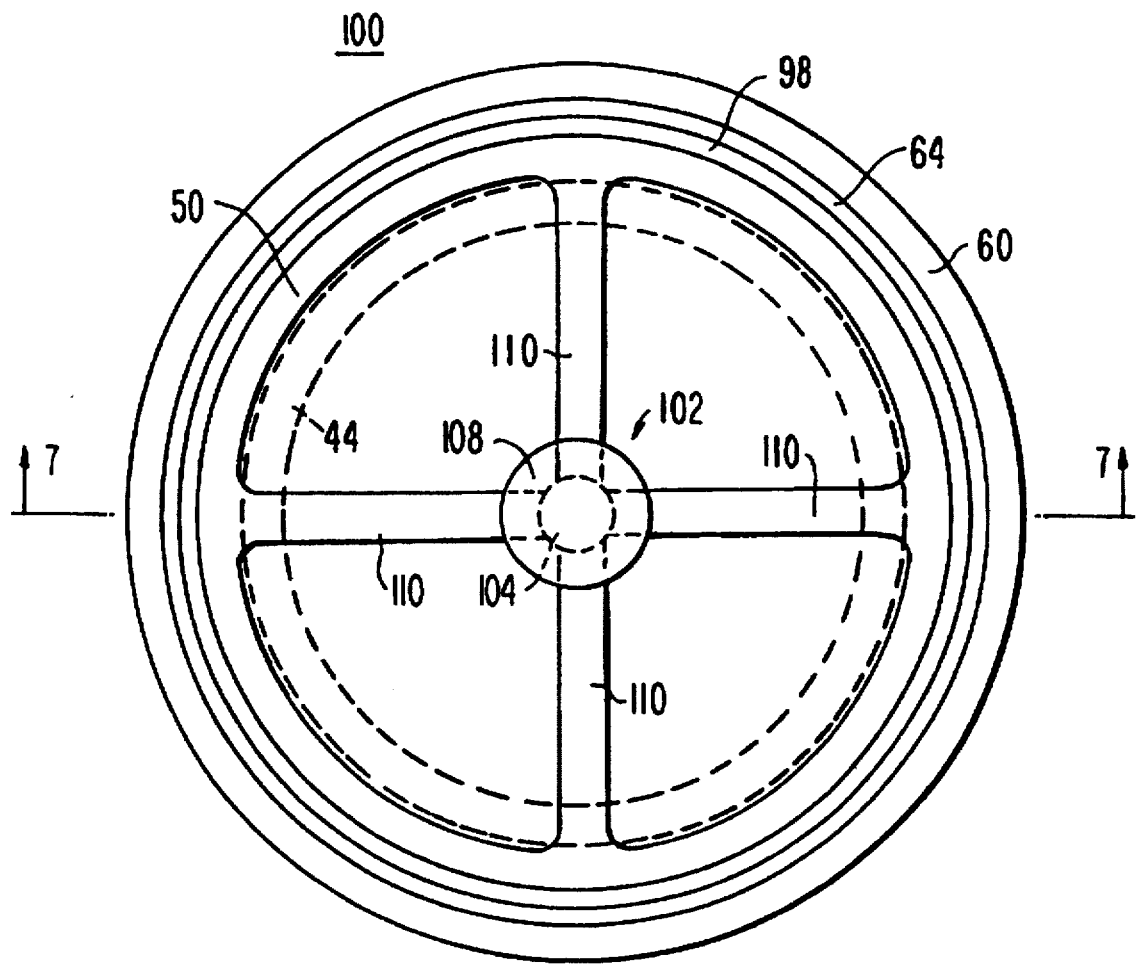
FIG. 6 illustrates a top view of another embodiment of a double open-ended sample holder in accordance with the present invention.
Figure 7:
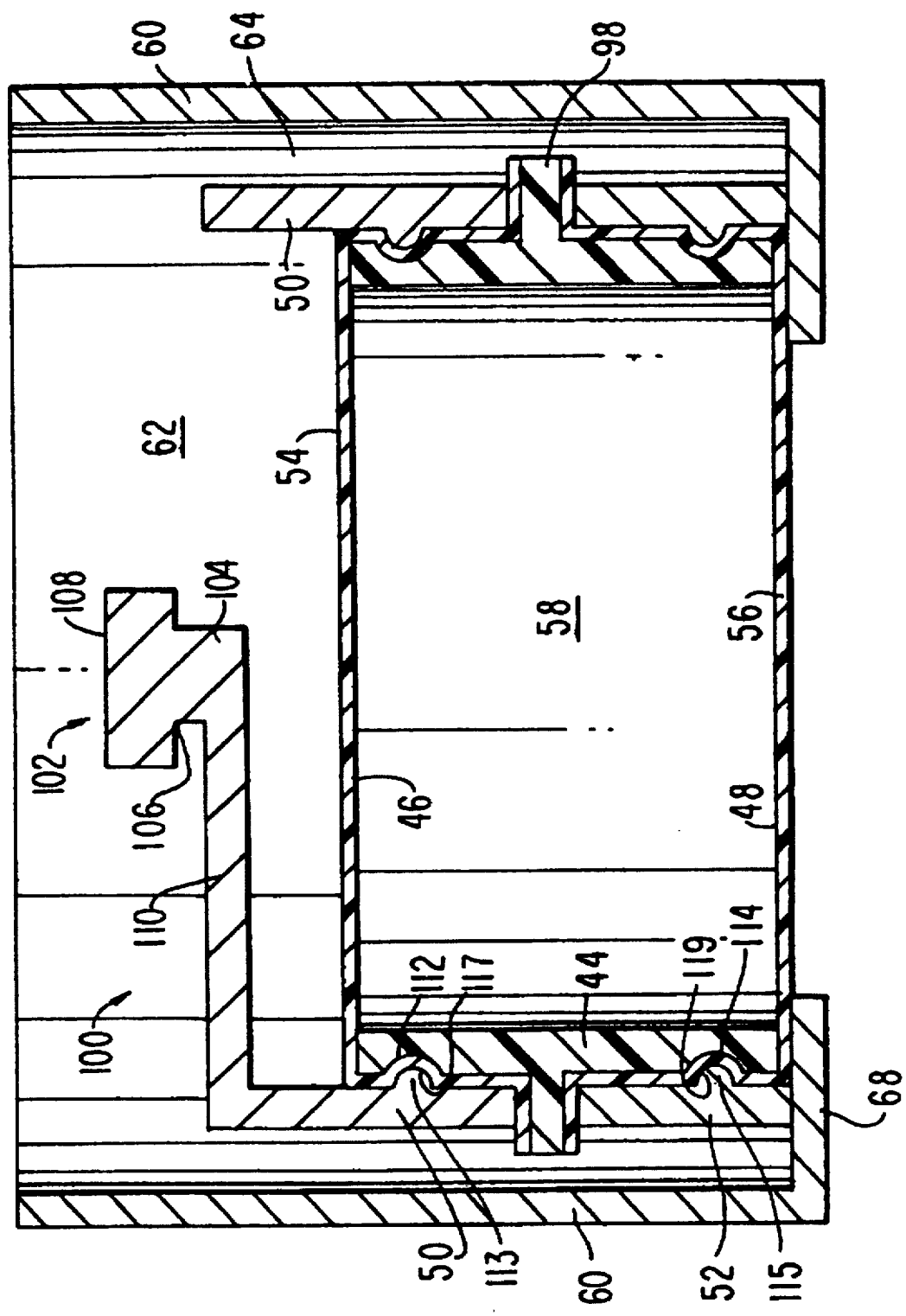
FIG. 7 is a sectional view taken through line 7—7 of FIG. 6.

FIGS. 6 and 7 illustrate another embodiment of the invention that includes a double open-faced sample holder 100 having features analogous to sample holder 40 with similar elements indicated by the same numerals as shown for sample holder 40. Sample holder 100 includes a handling support 102 that includes a cylindrical stem 104 having a top side 106 and a cylindrical disc 108 affixed to top side 106. Disc 108 has a greater diameter than the diameter of stem 104. Disc 108, stem 104, and cell wall 44 are vertically axially aligned. Stem 104 and disc 108 are spaced above top face 46 of cell compartment 58. Four horizontal support struts 110 are connected to and radiate outwardly at equal angles from stem 104 and connect to upper ring outer rim 80. Handling support 102, in particular struts 110, is positioned at such a distance above top face 46 of cell compartment 58 and microporous film 54 that a maximum area of microporous film 54 is available to pass gases generated by X-rays 42 striking sample material 42 in cell 58 (not shown). In addition, handling support 102 is spaced at such a distance above microporous film 54 so as to receive a lifting tool that will not interfere physically with the integrity of the film face of microporous film 54.

Upper and lower rings 50 and 52 are prevented from axial movement towards top and bottom faces 46 and 48, respectively, by upper and lower circumferential snap-in connections 112 and 114, respectively, each comprising a circumferential bead 113, 115 about each upper and lower ring 50 and 52, respectively, positioned respectively in a circumferential groove 117, 119 located in outer surface 72 of cell wall 44.

Figure 8:
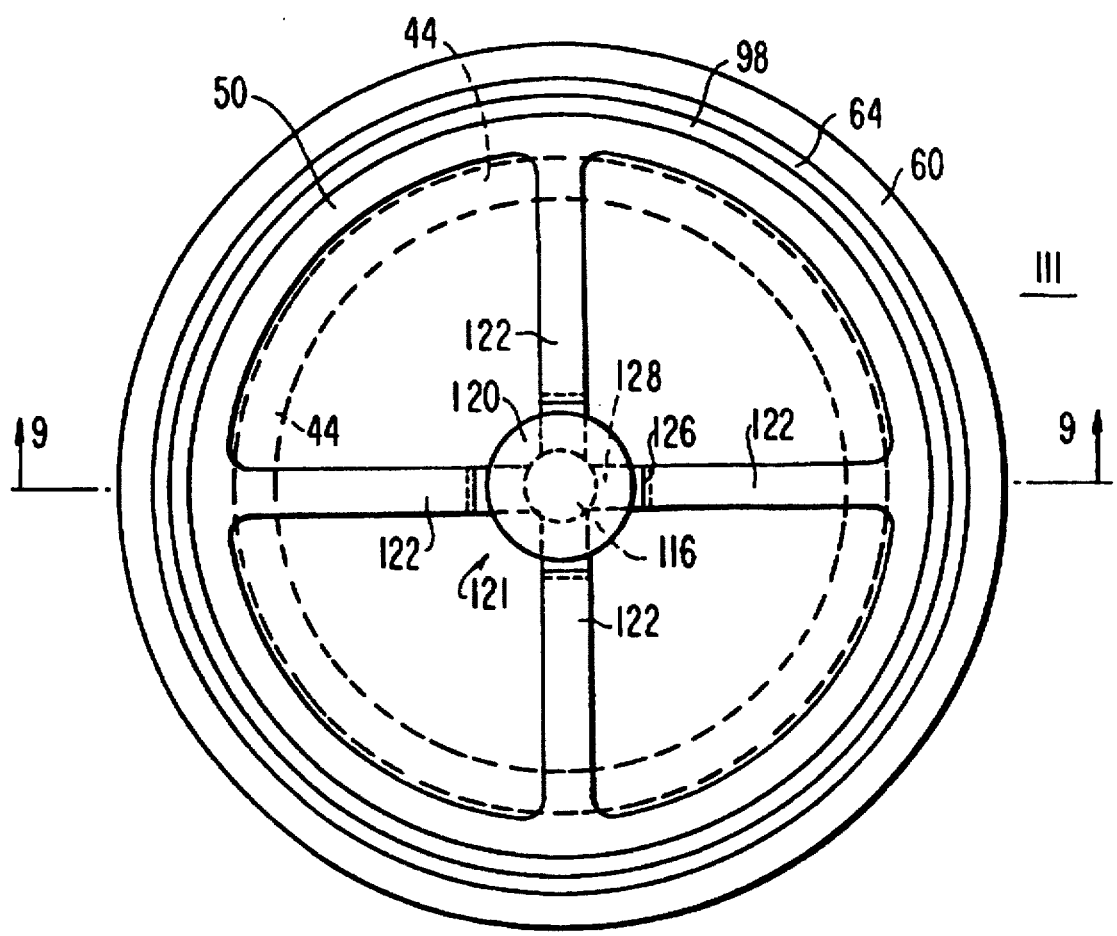
FIG. 8 illustrates a top plan view of another embodiment of a double open-ended sample holder in accordance with the present invention.
Figure 9:
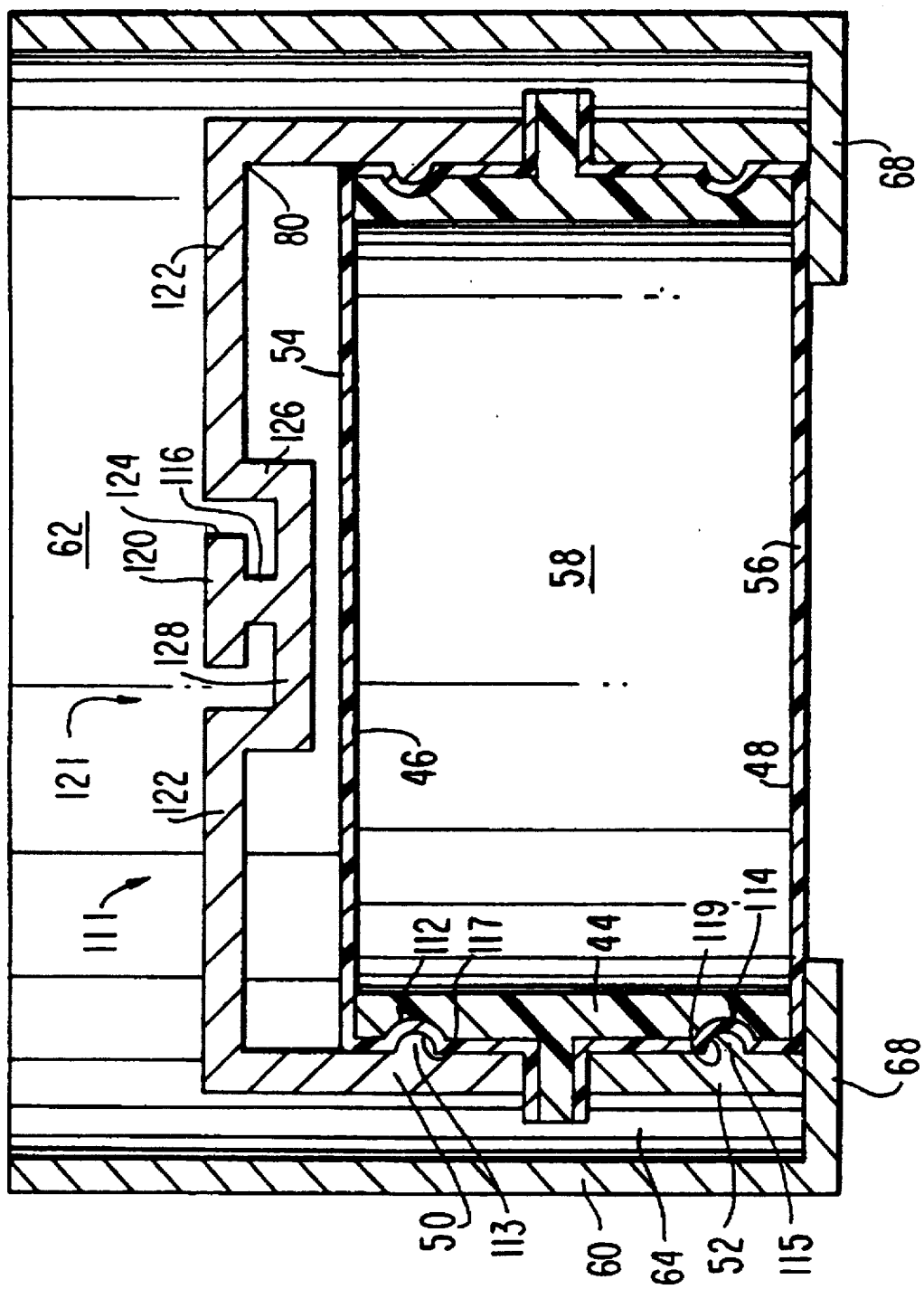
FIG. 9 is a sectional view taken through line 9—9 of FIG. 8.

FIGS. 8 and 9 illustrate another embodiment of the invention that includes a double open-faced sample holder 111 having features analogous to sample holder 100 illustrated in FIGS. 6 and 7 with similar elements indicated by the same numerals as shown for sample holder 100. Sample holder 111 includes a handling support 121 that includes a cylindrical stem 116 having a top side and a cylindrical disc 120 affixed thereto. Disc 120 has a greater diameter than the diameter of stem 116. Disc 120, stem 116, and cell wall 44 are vertically axially aligned. Stem 116 and disc 120 are spaced above top face 46 of cell compartment 58. Four support struts 122 are connected to and radiate horizontally at equal angles from upper ring outer rim 80 to an axial area where struts 122 extend downwardly by way of vertical strut portions 126 to a position spaced above microporous film 54 to form an axially aligned well 124 in which handling support 114 is positioned. Short horizontal tie-in struts 128 connect strut portions 126 with stem 116. Handling support 114, which includes struts 122, well 124 and stem 116 with disc 120 are positioned at a such a distance above top face 46 of cell compartment 58 and microporous film 54 that a maximum area of microporous film 54 is available to pass gases generated by X-rays striking sample material in cell 58 (not shown). In addition, handling support 121 is spaced at such a distance above microporous film 54 so as to receive a lifting tool that will not interfere physically with the integrity of the film face of microporous film 54.

Upper and lower rings 50 and 52 are prevented from axial movement towards top and bottom faces 46 and 48, respectively, by upper and lower circumferential snap-in connections 112 and 114, respectively, each comprising a circumferential bead 113, 115 about upper and lower ring 50 and 52, respectively, positioned in a circumferential groove 117, 119, respectively, located in outer surface 72 of cell wall 44 adjacent rings 50 and 52, respectively.

Figure 10:
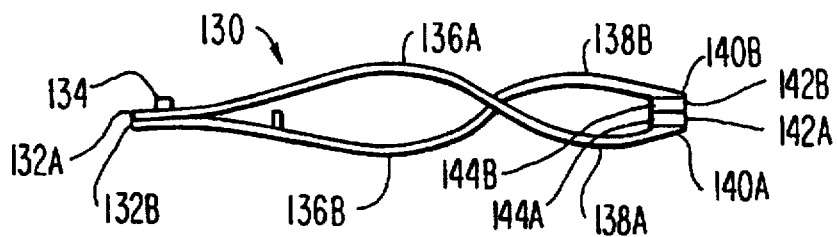
FIG. 10 is a top plan view of a tool for remote handling of the sample holder in accordance with the present invention.
Figure 11:
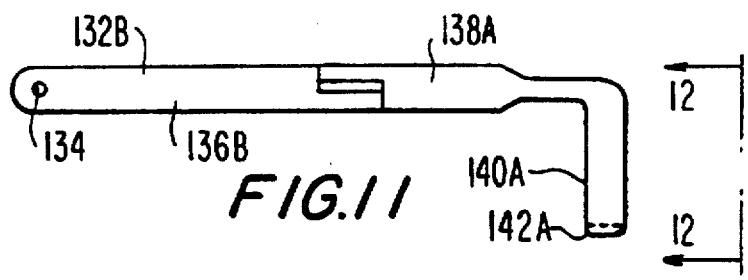
FIG. 11 is a side elevational view of the tool shown in FIG. 10.
Figure 12:
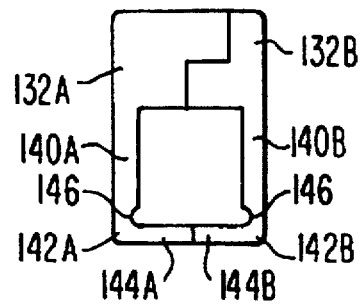
FIG. 12 is an end elevational view of the tool shown in FIG. 11.

FIGS. 10, 11, and 12 illustrate a remote support handling tool, namely, tweezers 130, that can be used to grasp and to lower sample holder 40 into and subsequently to raise sample holder 40 from cassette 60 (See FIG. 4). A pair of opposed, biased horizontal arms 132A and 132B are joined at one end by a rivet 134. Arms 132A and 132B have first outward convolutions 136A and 136B from rivet area 134 then convoluted back in a crossover to second outward convolutions 138A and 138B and then return to opposed vertical fingers 140A and 140B that terminate in pinching portions or jaws 142A and 142B which have opposed inner shelves 144A and 144B that fit under support bar 92 for lifting sample holder 40 when placing sample holder 40 into cassette 60 or removing sample holder 40 from cassette 60. Opposed cutouts 146 are defined by jaws 142A and 142B at shelves 144A and 144B. When first outward convolutions 136A and 136B are manually or remotely pressed together, jaws 142A and 142B and shelves 144A and 144B are forced apart with arms 132A and 132B in a biased mode. When first convolutions 136A and 136B are released, arms 132A and 132B self-biasedly move to a lesser biased mode so as to hold jaws 142A and 142B together. Support bar 92 lies upon shelves 144A and 144B with the sides of support bar 92 positioned in cutouts 146.

Figure 13:
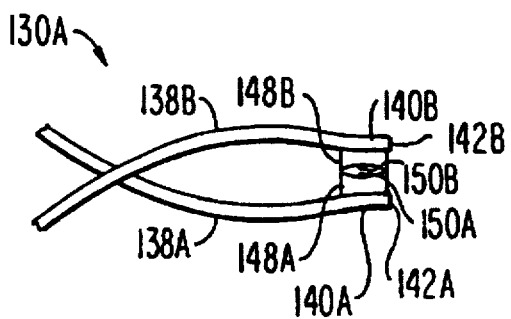
FIG. 13 is a top plan of the tool shown in FIG. 10 showing an alternative embodiment of the tool.

FIG. 13 illustrates a tweezers 130A that has opposed shelves 148A and 148B that each define a semicircular aperture 150A and 150B and which receive stems 104 and 116 of handling supports 102 and 114. Shelves 148 are in contact with the underside of discs 108 and 120 so that sample holders 100 and 112 can be raised or lowered by manipulation of tweezers 130A.

Figure 14:
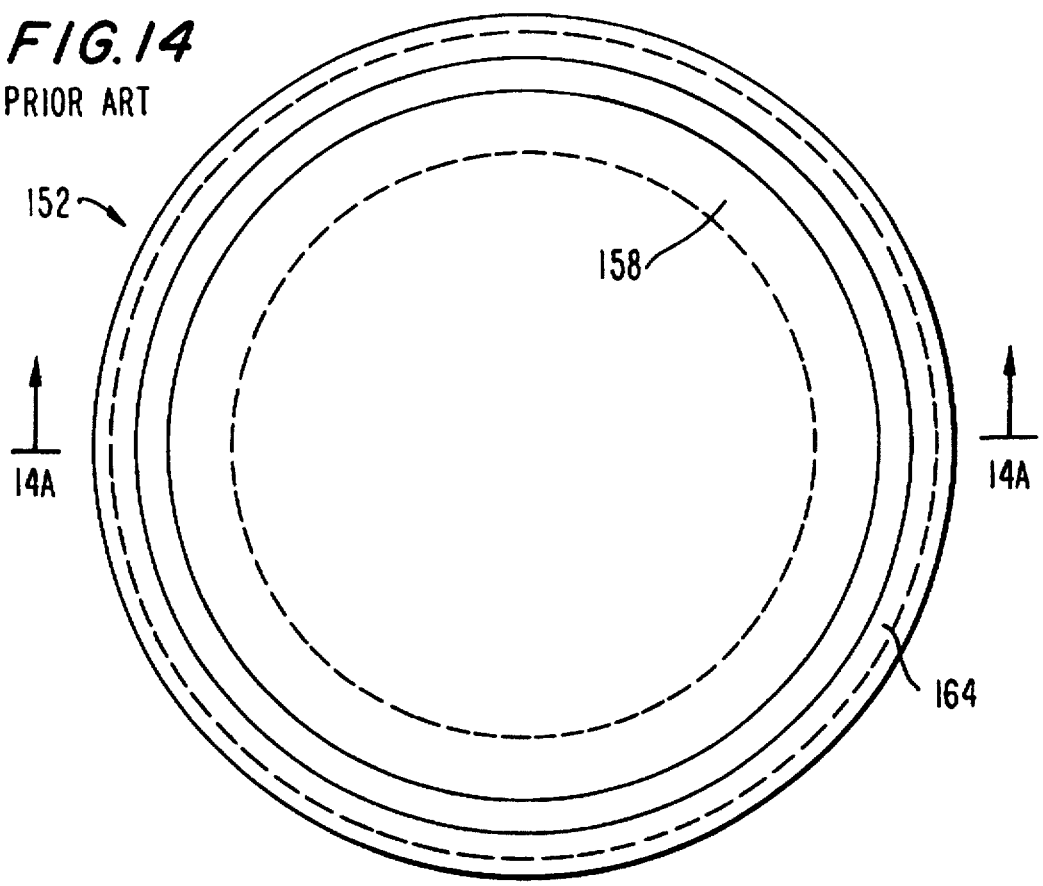
FIG. 14 illustrates a top plan view of a prior art double open-ended sample holder.
Figure 14A:
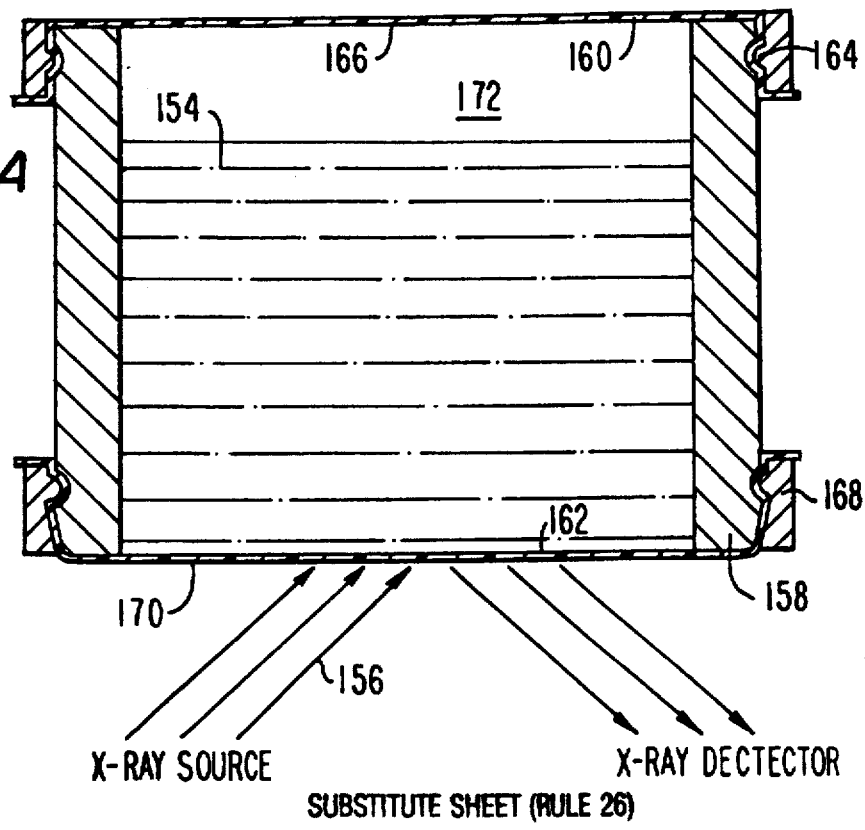
FIG. 14A is a view taken through line 14A—14A of FIG. 14.

FIGS. 14 and 14A illustrate a prior art double open-ended sample holder 152 holding sample material 154, which can be a liquid or powder, shown here as a liquid, positioned for inverted optics X-ray spectroscopic analysis. Sample material 154 is of a nature that X-rays 156 generate heat therein resulting in the creation of a gas containing contaminants that must not be allowed to pass from sample holder 152. At the same time, a pressure buildup in sample holder 152 must be avoided. Sample holder 152 includes a cylindrical wall 158 having a top open face 160 and an opposed bottom open face 162 and an upper cylindrical ring 164 securing an upper thin plastic protective film, either microporous or solid film, 166 to wall 158 across top open face 160 and a lower cylindrical ring 168 securing a lower thin plastic analytic film 170 across bottom face 162 so as to define a sample holder cell 172. Sample holder 152 can be positioned in the cylindrical compartment of an X-ray cassette for an X-ray spectroscopic apparatus in preparation for upright optics X-ray analysis with the X-ray source being below sample holder 152. X-rays 156 entering through lower analytic film 170 strike sample material 154 at an angle and return to the X-ray detector for analysis. The cassette is typically of the type shown in FIG. 1. Liquids upon heating during analysis can flow across the outer surface of microporous or solid film 166 and ultimately onto sample holder 152 and the sample holder cassette and ultimately onto the X-ray apparatus.

Figure 15:
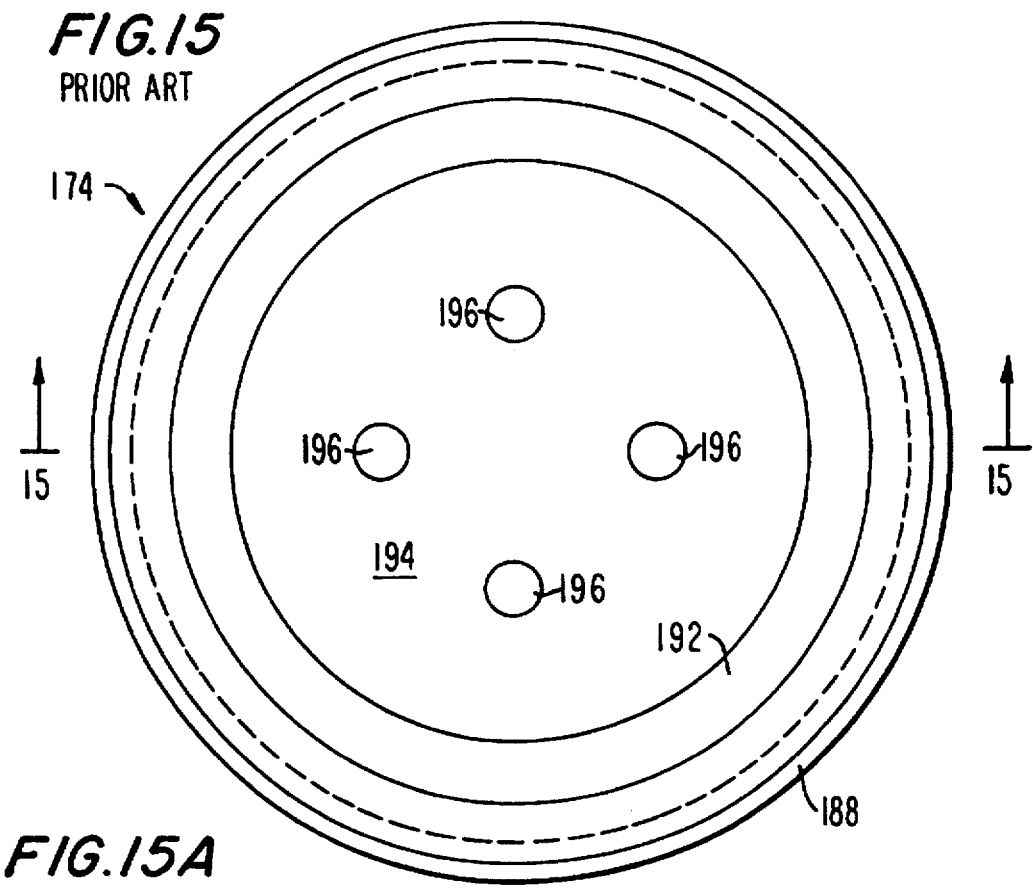
FIG. 15 illustrates a top plan view of a prior art sample holder with a compartment.
Figure 15A:
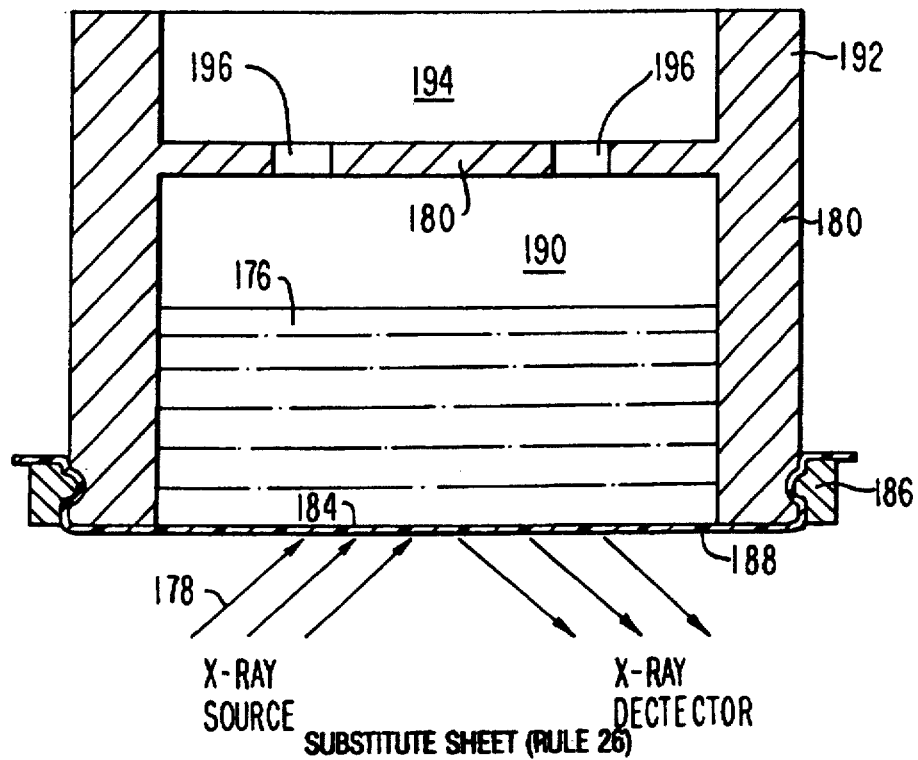
FIG. 15A is a view taken through line 15A–15A of FIG. 15.

FIGS. 15 and 15A illustrate a prior art sample holder 174 holding sample material 176 which can be a liquid or powder, shown here as a liquid for X-ray spectroscopic analysis, is illustrated in FIGS. 15 and 15A. Sample material 176 is of a nature that X-rays 178 generate heat therein resulting in the creation of a gas containing contaminants that must not be allowed to pass from sample holder 174. At the same time, a pressure buildup in sample holder 174 must be avoided. Sample holder 174 includes a cylindrical wall 180 having a top horizontal wall 182 unitary with cylindrical wall 180 and an opposed bottom open face 184 and a lower cylindrical ring 186 securing a lower thin plastic analytic film 188 across bottom face 184 so as to define a sample holder cell 190. Cylindrical wall 180 includes a cylindrical upper portion 192 that together with horizontal wall 182 defines a reservoir, or compartment, 194. After film 188 has been mounted across face 184, turned over, cell 190 filled with sample material 176, and once again turned over, a plurality of holes, shown as four holes 196, are punched through horizontal wall 182. Sample holder 174 can be positioned in the cylindrical compartment of an X-ray cassette for an X-ray spectroscopic apparatus in preparation for upright optics X-ray analysis with X-ray source being positioned below sample holder 174. X-rays 178 enter through lower analytic film 188 to strike sample. material 176 at an angle and return to the X-ray detector for analysis. The cassette is typically of the type shown in FIG. 1. Liquids upon heating during analysis can flow through holes 196 into compartment 194, where such liquid will be contained and prevented from contaminating the cassette. As noted previously, the disadvantage of the latter sample holder is that the process of loading is particularly a problem when the sample holder is full; mishaps are always a possibility. In addition, without microporous or solid film, substances are free to pass through punch holes 196.

Figure 16:
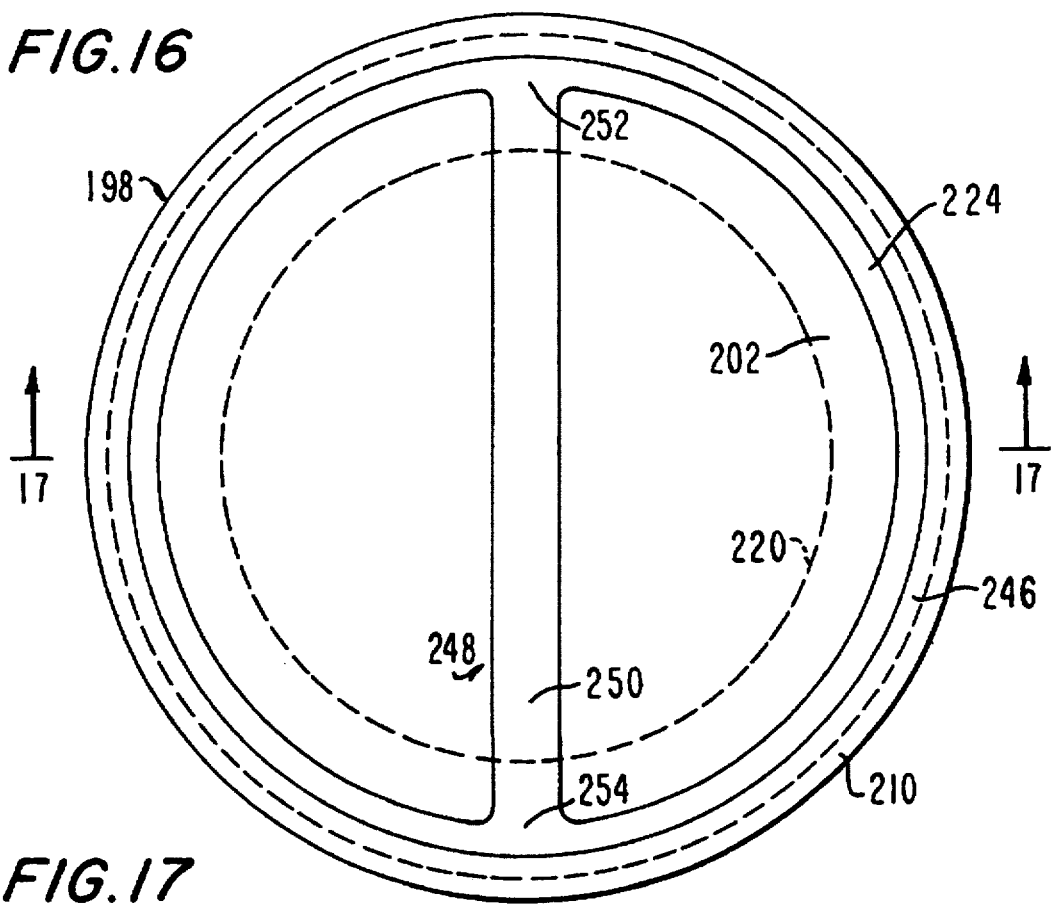
FIG. 16 illustrates a top plan view of a double open-ended sample older with a ring mounting a protective microporous or solid film in accordance with the present invention the ring defying a compartment with a handling support.
Figure 17:
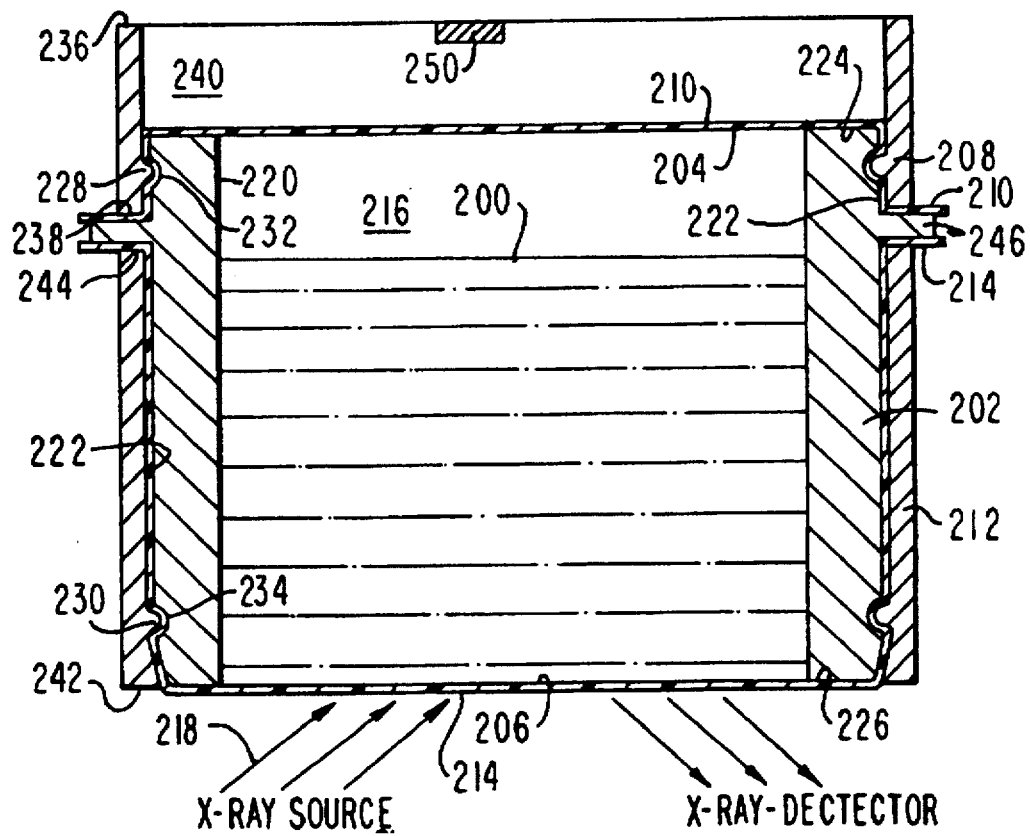
FIG. 17 is a view taken through line 16—16 of FIG. 16.

In accordance with the present invention, FIGS. 16 and 17 illustrate a double open-ended sample holder 198 holding sample material 200, which can be a powder or a liquid, shown here as a liquid, positioned for inverted optics X-ray spectroscopic analysis. Sample holder 198 includes an upright cylindrical cell wall 202 having a top open face 204 and an opposed bottom open face 206 and an upper cylindrical ring 208 securing an upper microporous or solid film 210 laterally across top open face 204 to cell wall 202 and a lower cylindrical ring 212 securing a lower analytic film 214 tautly and laterally across bottom open face 206 to cell wall 202 so as to define a sample holder cell 216 in which sample material 200 is located. Sample holder 198 is positioned in a cassette (not shown) analogous to cassette 60 shown in FIGS. 3 and 4, for an X-ray spectroscopic apparatus with X-rays 218 entering through analytic film 214 from the bottom side of sample holder 198 through a circular open area defined across the bottom of the cassette to strike sample material 200 at an angle and returning to the X-ray detector for analysis.

Cylindrical cell wall 202 has inner and outer surfaces 220 and 222, respectively, and opposed cell wall circular top and bottom rims 224 and 226, respectively, that define opposed top and bottom faces 204 and 206, respectively. Upper microporous or solid film 210, which is positioned across top open face 204 of cell 216, passes gas from cell 216 resulting from heat generated in sample material 200 by X-rays 218 and simultaneously prevents harmful particle materials from passing out of cell 216. Lower analytic film 214 is positioned across bottom open face 206 of cell 216 and lower ring 212 maintains a taut film surface for sample material 200 in contact therewith for X-ray analysis.

Upper and lower rings 208 and 212 are prevented from axial movement towards top and bottom faces 204 and 206, respectively, by upper and lower circumferential snap-in connections, respectively, each comprising respectively a circumferential bead 228, 230 about upper and lower rings 208 and 212, respectively, in a circumferential groove 232, 234, respectively, located in outer surface 222 of cell wall 202.

Upper ring 208 is mounted to cell wall 202 at outer cylindrical surface 222. Upper ring 208 has upper ring circular outer and inner rims 236 and 238, respectively. Upper ring 208 mounts protective microporous or solid film 210 to cell wall 202 wherein microporous or solid film 210 extends across top open face 204 and is pressed between outer surface 222 and the inner surface of upper ring 208. Upper ring outer rim 236 is spaced above cell wall top rim 224 so that a continuous ring wall extends outwardly from and perpendicular to top open face 204 from cell wall top rim 224 that together with microporous or solid film 210 extending across top open face 204 defines a reservoir, or compartment 240. Compartment 240 retains overflow sample material that passes through microporous or solid film 210, thus protecting the cassette and the X-ray apparatus from contamination.

Lower ring 212 mounts analytic film 214 to cell wall 202 wherein analytic film 214 extends across bottom open face 206 and is pressed between outer surface 222 of cell wall 202 and the inner surface of lower ring 212. Lower ring 212 has outer and inner rims 240 and 242, respectively, with outer rim 240 being generally aligned with cell wall bottom rim 226 and bottom open face 206.

A circular stop flange 246 extending outwardly from outer surface 222 of cylindrical cell wall 202 seats upper ring 208 at upper ring inner rim 238 relative to cell wall 202 during the mounting process and in addition prevents movement in an axial direction towards bottom face 206 after seating. Stop flange 246 also seats lower ring 212 at lower ring inner rim 244 relative to cell wall 202 during the mounting process and in addition prevents axial movement in a direction towards top face 204 after seating.

A handling support 248 is connected to upper ring outer rim 236 and spaced above top face 204 of cell 216. Handling support 248 provides a grip for a tool used in the process of gentle placement or removal of sample holder 198 from the cassette in which sample holder 198 is positioned. Handling support 248 includes a support bar 250 attached at opposed ends 252 and 254 to upper ring outer rim 236 extending diametrically across and horizontally spaced above top face 204 of cell 216 so that the entire area of microporous or solid film 210 is available to pass gases generated by X-rays 218 striking sample material 200 in cell 216. In addition, support bar 250 is spaced at a distance above microporous or solid film 210 without interfering with the integrity of the face of microporous or solid film 210. In addition, support bar 250 is spaced at such a distance above microporous or solid film 210 so as to receive a lifting tool that will not interfere physically with the integrity of the film face of microporous or solid film 210.

Inner rim 238 of upper ring 208 is spaced at such a distance from outer rim 236 of upper ring 208 and is of such a thinness that inner rim 238 is both flexible and resilient so that microporous or solid film 210 can be mounted to cell wall 202 gently and securely without being damaged or torn. Lower ring 212 has both the flexibility and resilience to gently mount analytic film 214 and to hold analytic film 214 firmly and tautly across bottom face 206. Upper and lower rings 208 and 212 are made of resilient plastic.

In accordance with another embodiment of the present invention illustrated in FIGS. 18 and 19, a double open-ended sample holder 256 holding sample material 258, which can be a powder or a liquid, shown here as a liquid, positioned for inverted upright optics X-ray spectroscopic analysis is illustrated in FIGS. 18 and 19. Sample holder 256 includes a vertical cylindrical cell wall 260 having a top open face 262 and an opposed bottom open face 264 and an upper cylindrical ring 266 securing an upper microporous film 268 laterally across top open face 262 to cell wall 260 and a lower cylindrical ring 270 securing a lower analytic film 272 tautly and laterally across bottom open face 264 to cell wall 260 so as to define a sample holder cell 274 in which sample material 258 is located. Sample holder 256 is positioned in a cassette (not shown) analogous to cassette 60 shown in FIGS. 3 and 4, for an upright optics X-ray spectroscopic apparatus with X-rays 276 entering through analytic film 272 from the bottom side of sample holder 256 through a circular open area defined across the bottom of the cassette to strike sample material 258 at an angle and returning to the X-ray detector for analysis.

Cylindrical cell wall 260 has inner and outer surfaces 278 and 280, respectively, and opposed cell wall circular top and bottom rims 282 and 284, respectively, that define opposed top and bottom faces 262 and 264, respectively. Upper microporous film 268, which is positioned across top open face 262 of cell 274, passes gas from cell 274 resulting from heat generated in sample material 258 by X-rays 276 and simultaneously prevents harmful particle materials from passing out of cell 274. Lower analytic film 272 is positioned across bottom open face 264 of cell 274 and lower ring 270 maintains a taut film surface for sample material 258 in contact therewith for X-ray analysis.

Upper and lower rings 266 and 270 are prevented from axial movement towards top and bottom faces 262 and 264, respectively, by upper and lower circumferential snap-in connections, respectively, each comprising respectively a circumferential bead 286, 288 about upper and lower rings 266 and 270, respectively, in a circumferential groove 290, 292, respectively, located in outer surface 280 of cell wall 260.

Upper ring 266 is mounted to cell wall 260 at outer cylindrical surface 280. Upper ring 266 has upper ring circular outer and inner rims 294 and 296, respectively. Upper ring 266 mounts microporous film 268 to cell wall 260 wherein microporous film 268 extends across top open face 262 and is pressed between outer surface 278 and the inner surface of upper ring 266. Upper ring outer rim 294 is spaced above cell wall top rim 282 so that a continuous ring wall extends outwardly from and perpendicular to top open face 262 from cell wall top rim 282 that together with microporous film 268 extending across top open face 262 defines a reservoir, or compartment 300. Compartment 300 retains overflow sample material that passes through the microporous film 268, thus protecting the cassette and the X-ray apparatus from contamination.

Lower ring 270 mounts analytic film 272 to cell wall 260 wherein analytic film 272 extends across bottom open face 264 and is pressed between outer surface 280 of cell wall 260 and the inner surface of lower ring 270. Lower ring 270 has outer and inner rims 302 and 304, respectively, with outer rim 302 being generally aligned with cell wall bottom rim 284 and bottom open face 264.

A circular stop flange 306 extending outwardly from outer surface 280 of cylindrical cell wall 260 seats upper ring 266 at upper ring inner rim 296 relative to cell wall 260 during the mounting process and in addition prevents movement in an axial direction towards bottom face 264 after seating. Stop flange 306 also seats lower ring 270 at lower ring inner rim 304 relative to cell wall 260 during the mounting process and in addition prevents axial movement in a direction towards top face 262 after seating.

Inner rim 296 of upper ring 266 is spaced at such a distance from outer rim 294 of upper ring 266 and is of such a thinness that inner rim 296 is both flexible and resilient so that microporous film 268 can be mounted to cell wall 260 gently and securely without being damaged or torn. Lower ring 270 has both the flexibility and resilience to gently mount analytic film 272 and to hold analytic film 272 firmly and tautly across bottom face 264. Upper and lower rings 266 and 270 are made of resilient plastic.

Figure 20:
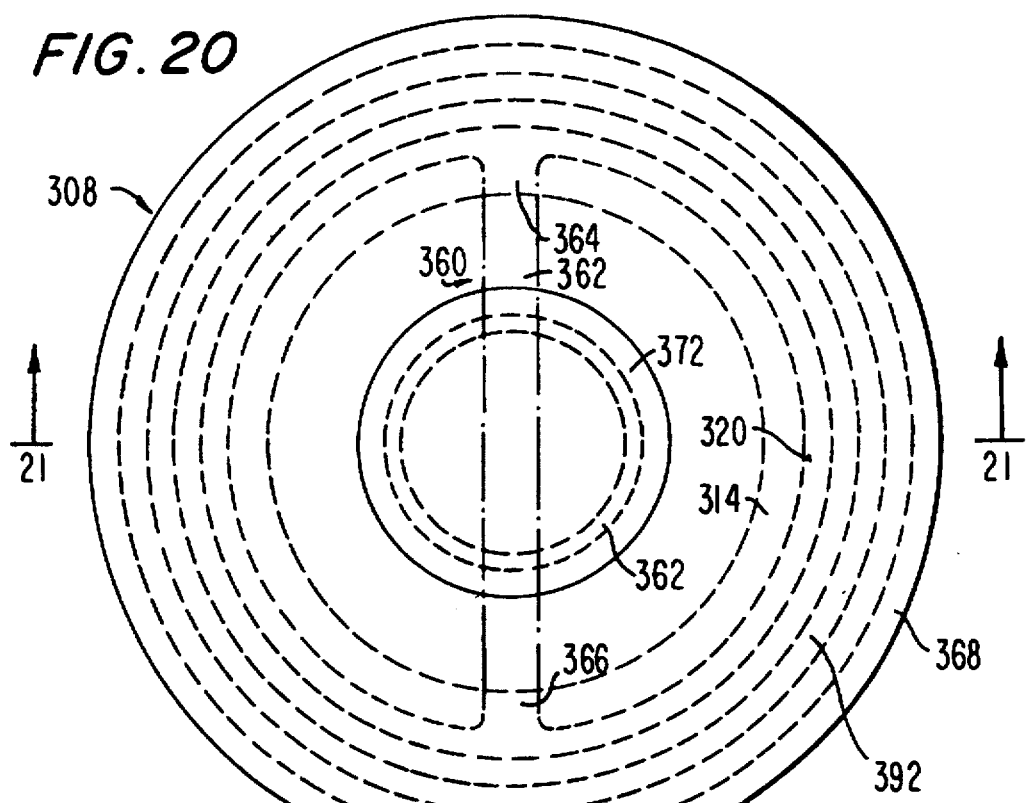
FIG. 20 illustrates a top plan view of a double open-ended sample holder with a ring mounting a microporous film defining a compartment mounted in a cassette in position for upright optics X-ray analysis and positioned in an upright protective cup.
Figure 21:
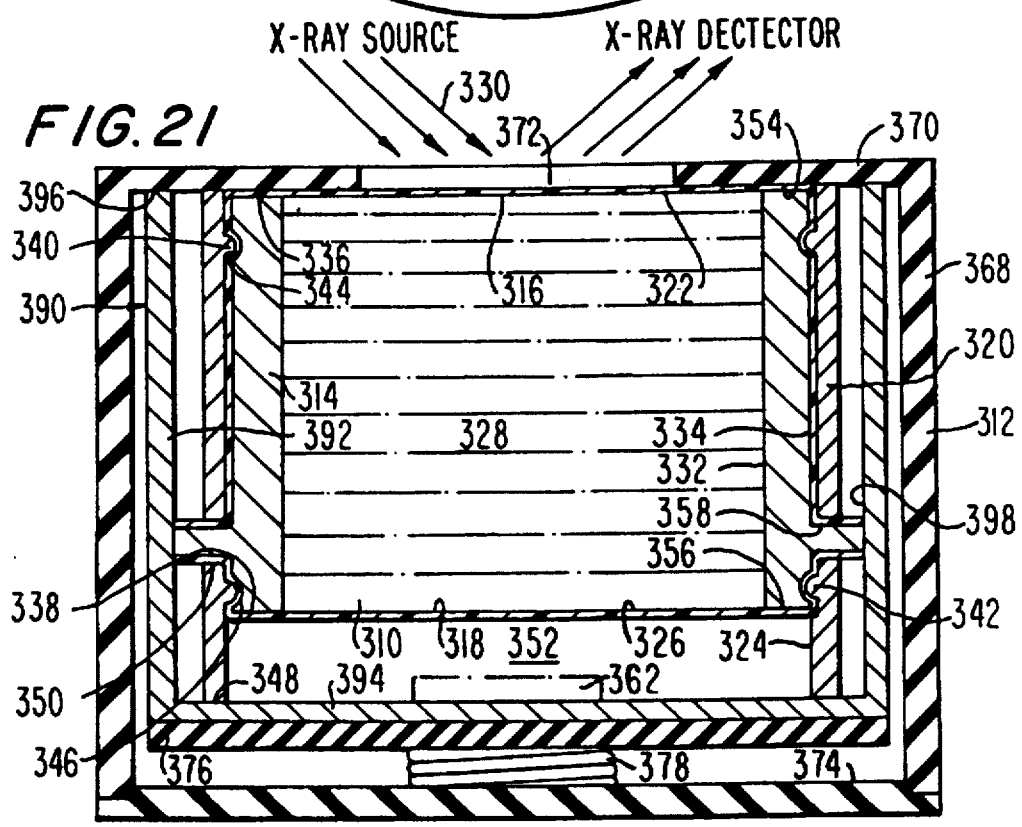
FIG. 21 is a view taken through line 21—21 of FIG. 20.

In accordance with another embodiment of the present invention, FIGS. 20 and 21 illustrate a double open-ended sample holder 308 holding sample material 310, which can be a powder or a liquid, shown here as a liquid, positioned in a cassette 312 for upright optics X-ray spectroscopic analysis. Sample holder 308 includes a vertical cylindrical cell wall 314 having a top open face 316 and an opposed bottom open face 316 and an upper cylindrical ring 320 securing an upper analytic film 322 laterally across top open face 316 to cell wall 314 and a lower cylindrical ring 324 securing a lower microporous film 326 tautly and laterally across bottom open face 318 to cell wall 314 so as to define a sample holder cell 328 in which sample material 310 is located. Sample holder 308 is positioned in cassette 312 positioned for upright optics X-ray spectroscopic apparatus with X-rays 330 entering through upper analytic film 322 from the top side of cassette 312 and sample holder 308 through a circular open area defined across the top of cassette 312 to strike sample material 310 at an angle and returning to the upper X-ray detector for analysis.

Cylindrical cell wall 314 has inner and outer surfaces 332 and 334, respectively, and opposed cell wall circular top and bottom rims 336 and 338, respectively, that define opposed top and bottom faces 316 and 318, respectively. Lower microporous film 326, which is positioned across bottom open face 318 of cell 328, passes gas from cell 328 resulting from heat generated in sample material 310 by X-rays 330 and simultaneously prevents harmful particle materials from passing out of cell 328. Upper analytic film 322 is positioned across top open face 316 of cell 328 and upper ring 320 maintains a taut film surface for sample material 310 in contact therewith for X-ray analysis.

Upper and lower rings 320 and 322 are prevented from axial movement towards top and bottom faces 316 and 318, respectively, by upper and lower circumferential snap-in connections, respectively, each comprising respectively a circumferential bead 340, 342 about the inner surfaces of upper and lower rings 320 and 324, respectively, in a circumferential groove 344, 346, respectively, located in outer surface 334 of cell wall 314.

Upper ring 320 is mounted to cell wall 314 at outer cylindrical surface 334. Lower ring 324 has lower ring circular outer and inner rims 348 and 350, respectively. Lower ring 324 mounts microporous film 326 to cell wall 314 wherein microporous film 326 extends across bottom open face 318 and is pressed between outer surface 334 and the inner surface of lower ring 324. Lower ring outer rim 348 is spaced below cell wall bottom rim 338 so that a continuous ring wall extends outwardly from and perpendicular to bottom open face 318 from cell wall bottom rim 338 that together with microporous film 326 extending across bottom open face 318 defines a reservoir, or compartment 352. Compartment 352 retains overflow sample material that passes through microporous film 326, thus protecting cassette 312 and the X-ray apparatus from contamination.

Upper ring 320 mounts analytic film 322 to cell wall 314 wherein analytic film 322 extends across top open face 316 and is pressed between outer surface 334 of cell wall 314 and the inner surface of upper ring 320. Upper ring 320 has outer and inner rims 354 and 356, respectively, with outer rim 354 being generally aligned with cell wall bottom rim 338 and bottom open face 318.

A circular stop flange 358 extending outwardly from outer surface 334 of cylindrical cell wall 314 seats upper ring 320 at upper ring inner rim 356 relative to cell wall 314 during the mounting process and in addition prevents movement in an axial direction towards bottom face 318 after seating. Stop flange 358 also seats lower ring 324 at lower ring inner rim 350 relative to cell wall 314 during the mounting process and in addition prevents axial movement in a direction towards top face 316 after seating.

An optional handling support 360 shown in phantom line is connected to lower ring outer rim 348 and spaced from bottom face 318 of cell 328. Handling support 360 provides a grip for a tool used in the process of gentle placement or removal of sample holder 308 from cassette 312 in which sample holder 308 is positioned. Handling support 360 includes a support bar 362 attached at opposed ends 364 and 366 to lower ring outer rim 348 extending diametrically across and horizontally spaced from bottom face 318 of cell 328 so that the entire area of microporous film 326 is available to pass gases generated by X-rays 330 striking sample material 310 in cell 328. In addition, support bar 362 is spaced at a distance from microporous film 326 without interfering with the integrity of the face of microporous film 326. In addition, support bar 362 is spaced at such a distance from microporous film 326 so as to receive a lifting tool that will not interfere physically with the integrity of the film face of microporous film 326.

Inner rim 350 of lower ring 324 is spaced at such a distance from outer rim 348 of lower ring 324 and is of such a thinness that inner rim 350 is both flexible and resilient so that microporous film 326 can be mounted to cell wall 314 gently and securely without being damaged or torn. Upper ring 320 has both the flexibility and resilience to gently mount analytic film 322 and to hold analytic film 322 firmly and tautly across top face 316. Upper and lower rings 320 and 324 are made of resilient plastic.

Cassette 312 is of a kind typically used for upright optics X-ray spectroscopic analysis and includes a vertical cylindrical wall 368, a horizontal top wall 370 having a circular aperture 372 axially aligned with cylindrical wall 368, and a circular bottom cap 374 screwed onto cylindrical wall 368 together forming a cassette cell in which cylindrical sample holder 308 is positioned in axial alignment. Cassette 312 includes a horizontal pressure plate 376 attached to the inner side of bottom cap 374 by a spring 378. A cylindrical safety cup 390 having a cylindrical cup wall 392 connected to a horizontal bottom cup wall 394 forming a cup chamber containing sample holder 308 is positioned therein. Circular stop flange 358 is in contact with inner cylindrical surface 398 of safety cup 390. Cup cylindrical wall 392 has a circular upper rim 396 that is maintained in pressure contact with cup top wall 370 and cup bottom wall 394 is in contact with outer rim 348 of lower ring 324. Pressure plate 376 is spring pressured against cup bottom wall 394 so as to pressure lower ring 324 upward by way of outer rim 348 so as to maintain sample holder 308 close to the X-ray source. X-rays 330 pass through cassette aperture 372, pass through analytic film 322 to strike sample material 310, and return through aperture 372 to the X-ray detector. Microporous film 326 can expand into compartment 352 because of heating of sample material 310 during X-ray analysis as indicated by phantom line 398. In the event microporous film 326 breaks during X-ray analysis, sample material 310 will spill into and be contained in cup 390.

Although the present system has been described in some detail by way of illustration and example for purposes of clarity and understanding, it will, of course, be understood that various changes and modifications may be made in the form, details, and arrangements of the parts without departing from the scope of the invention set forth in the following claims.

What is claimed is:

1. A sample holder system for a sample material for X-ray spectroscopic analysis, comprising, in combination, cell means for containing the sample material and having first and second rims defining opposed first and second open faces, respectively, a first ring mounted to said cell means at said first open face, an analytic film secured to said cell means by said first ring across said first open face, a second ring mounted to said cell means at said second open face, said second ring including a continuous ring wall extending outwardly from said second rim and perpendicular to said second open face, and a protective film secured to said cell means by said second ring across said second open face, said continuous ring wall and said protective film defining a compartment adjoining said second open face, said compartment arranged to receive particles passed from said cell means through said protective film due to the heating of said sample material by X-rays.

2. The sample holder system according to claim 1, wherein said protective film is microporous film.

3. The sample holder system according to claim 2, wherein said sample holder system is used in an upright X-ray optics system and is positioned in a container, the container having opposed first and second sides, the first side being open and said second side having an aperture, the container including: a cap removably connected to the container at the first side; a pressure plate; biasing means connected to the cap and to the pressure plate for upwardly pressuring the pressure plate; said sample holder system further including an upright cup having a cup bottom wall with a cup bottom edge and a continuous upright cup wall connected to said cup bottom edge defining a cup chamber, said cell means being positioned in said cup chamber with said continuous wall of said second ring being in contact with said cup bottom wall and the pressure plate being in pressure contact with said cup bottom wall, said analytic film being located in an upside position during analysis proximate to the aperture and said microporous film being located in a downside position; whereby the microporous film can expand into said cup chamber during X-ray analysis and in the event the microporous film breaks during X-ray analysis the sample material will spill into and be contained in the cup chamber.

4. The sample holder system according to claim 1, wherein said protective film is solid film.

5. The sample holder system according to claim 1, further including handling support means for providing a grip for a tool used in the process of raising or lowering said sample holder, said handling support means being connected to said second ring and spaced away from said protective film.

\* \* \* \* \*